United States Patent
Weffers-Albu et al.

(10) Patent No.: US 11,129,549 B2
(45) Date of Patent: Sep. 28, 2021

(54) DEVICE, SYSTEM AND METHOD FOR PATIENT MONITORING TO PREDICT AND PREVENT BED FALLS

(71) Applicant: KONINKLIJKE PHILIPS N.V., Eindhoven (NL)

(72) Inventors: Mirela Alina Weffers-Albu, Boukoul (NL); Achim Gerhard Rolf Koerber, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 121 days.

(21) Appl. No.: 16/327,368

(22) PCT Filed: Aug. 21, 2017

(86) PCT No.: PCT/EP2017/071007
§ 371 (c)(1),
(2) Date: Feb. 22, 2019

(87) PCT Pub. No.: WO2018/036953
PCT Pub. Date: Mar. 1, 2018

(65) Prior Publication Data
US 2019/0192052 A1    Jun. 27, 2019

(30) Foreign Application Priority Data
Aug. 24, 2016 (EP) .................. 16185483

(51) Int. Cl.
*A61B 5/02* (2006.01)
*A61B 5/11* (2006.01)
(Continued)

(52) U.S. Cl.
CPC .......... *A61B 5/1117* (2013.01); *A61B 5/0205* (2013.01); *A61B 5/14542* (2013.01);
(Continued)

(58) Field of Classification Search
CPC ........ G16H 40/67; G16H 50/30; G16H 40/63; A61B 5/72; A61B 5/68; A61B 5/1117;
(Continued)

(56) References Cited

U.S. PATENT DOCUMENTS 10,692,011 B2 * 6/2020 Pathak .................. G06N 20/00
2003/0212579 A1 * 11/2003 Brown ................. A61B 5/7275
705/2

(Continued)

FOREIGN PATENT DOCUMENTS

WO    2010105203 A1    9/2010
WO    2015074007 A1    5/2015
(Continued)

OTHER PUBLICATIONS

Abbate, S. et al., "Monitoring of human movements for fall detection and activities recognition in elderly care using wireless sensor network: a survey", Dec. 2010.
(Continued)

*Primary Examiner* — Amanda K Hulbert
*Assistant Examiner* — Natasha Patel

(57) ABSTRACT

The present invention relates to a device (20) for detection of a vital signs related risk score (111) for a bed fall risk of an individual (2), the device (20) comprising a first port (3) for obtaining vital signs data (140) related to a vital sign of the individual (2) and a vital signs processing unit (9) for obtaining and processing the vital signs data (140) to generate a vital signs related risk score (111) indicating the bed fall risk of the individual (2) by detecting at least one risk factor from the vital signs data (140) and computing the vital signs risk score (111) from the at least one risk factor.

19 Claims, 11 Drawing Sheets

(51) Int. Cl.

| | | |
|---|---|---|
| *G16H 50/30* | (2018.01) | |
| *G16H 40/63* | (2018.01) | |
| *G16H 40/67* | (2018.01) | |
| *A61B 5/0205* | (2006.01) | |
| *A61B 5/145* | (2006.01) | |
| *A61B 5/16* | (2006.01) | |
| *A61B 5/00* | (2006.01) | |
| *A61B 5/021* | (2006.01) | |
| *A61B 5/024* | (2006.01) | |
| *A61B 5/08* | (2006.01) | |

(52) U.S. Cl.
CPC ............ *A61B 5/165* (2013.01); *A61B 5/7275* (2013.01); *A61B 5/746* (2013.01); *G16H 40/63* (2018.01); *G16H 40/67* (2018.01); *G16H 50/30* (2018.01); *A61B 5/021* (2013.01); *A61B 5/024* (2013.01); *A61B 5/02405* (2013.01); *A61B 5/02416* (2013.01); *A61B 5/0816* (2013.01); *A61B 2562/0219* (2013.01)

(58) Field of Classification Search
CPC ... A61B 5/0205; A61B 5/14542; A61B 5/165; A61B 5/7275; A61B 5/746; A61B 5/021; A61B 5/024; A61B 5/02405; A61B 5/02416; A61B 5/0816; A61B 2562/0219
See application file for complete search history.

(56) References Cited

U.S. PATENT DOCUMENTS

| | | | | |
|---|---|---|---|---|
| 2008/0186189 | A1* | 8/2008 | Azzaro | G16H 15/00 340/573.7 |
| 2011/0156915 | A1 | 6/2011 | Brauers et al. | |
| 2011/0301432 | A1* | 12/2011 | Riley | A61B 5/1115 600/300 |
| 2012/0132211 | A1 | 5/2012 | Halperin et al. | |
| 2013/0267791 | A1* | 10/2013 | Halperin | A61B 5/6892 600/300 |
| 2013/0303860 | A1* | 11/2013 | Bender | A61B 5/1117 600/300 |
| 2014/0259414 | A1* | 9/2014 | Hayes | A61G 7/018 5/611 |
| 2015/0302539 | A1* | 10/2015 | Mazar | G08B 21/0211 705/3 |
| 2018/0374581 | A1* | 12/2018 | Berringer | G16H 50/30 |

FOREIGN PATENT DOCUMENTS

| | | |
|---|---|---|
| WO | 2015079436 A1 | 6/2015 |
| WO | 2015143085 A1 | 9/2015 |

OTHER PUBLICATIONS

Li, Q. et al., "Accurate, Fast Fall Detection Using Gyroscopes and Accelerometer-Derived Posture Information", Body Sensor Networks, 2009.
Noury, N., "A Smart Sensor for the Remote Follow Up of Activity and Fall Detection of the Elderly", France, 2009.
Planinc et al, "Pattern Recognition (ICPR)", 2014, pp. 4234-4239.
Vrigkas et al, "Internal Conference on Computer Vision Theory and Applications", 2013, pp. 112-117.
Fook et al, "International Conference on e-Health Networking", 2007, pp. 68-73.
Todd C, Skelton D. (2004) "What are the main risk factors for falls among older people and what are the most effective interventions to prevent these falls?" Copenhagen, WHO Regional Office for Europe.
Halfon P, Eggli Y, Van Melle G, Vagnair A. "Risk of falls for hospitalized patients: a predictive model based on routinely available data". J Clin Epidemiol 2001;54(12):1258-66.
Hoidrup S, Sorensen Ti, Gronbaek M, Schroll M. Incidence and characteristics of falls leading to hospital treatment: a one-year population surveillance study of the Danish population aged 45 years and over. Scand J Public Health 2003;31(1):24-30.
Boushon B, Nielsen G, Quigley P, Rita S, Rutherford P, Taylor J, Shannon D, Rita S. Transforming Care at the Bedside How-to Guide: Reducing Patient Injuries from Falls. Cambridge, MA: Institute for Healthcare Improvement; 2012. Available at: www.ihi.org.
Morse J. Preventing Patient Falls. London: Sage Publications, 1996.
Oliver D, Seed P, Martin F. Preventing patient falls. Age Ageing 2002; 31: 75-6.
Oliver D, Britton M, Seed P. Development and evaluation of an evidence based risk assessment tool (STRATIFY) to predict which elderly inpatients will fall: case-control and cohort studies. Br Med J 1997; 315: 1049-53.
Oliver D., "Bed falls and bedrails—what should we do?" Age and Ageing 2002; 31: 415-418, 2002, British Geriatrics Society.
Agency for Healthcare Research and Quality, "Guidlines and Measures", http://www.guideline.gov/content.aspx?id=36906, Accessed Feb. 2019.
David Oliver, "Falls risk-prediction tools for hospital inpatients. Time to put them to bed?", Age Ageing (2008) 37(3): 248-250. doi: 10.1093/ageing/afn088.
Chu LW, Pei CK, Chiu A et al. Risk factors for falls in hospitalized older medical patients. J Gerontology 1999; 54: M38-48.
Gales BJ, Menard SM. Relationship between administration of selected medications and falls in hospitalised elderly patients. Ann Pharmacother 1995; 4: 354-7.
Gluck T, Wientjes H, Rai G. An evaluation of risk factors for inpatient falls in acute care and rehabilitation elderly care wards. Gerontology 1996: 42: 104-7.
Janken JK, Reynolds BA, Swiech K Patient falls in the acute care setting; identifying risk factors. Nursing Res 1986; 35: 215-19.
Lichtenstein MJ, GrifWn MR, Cornell JE. Risk factors for hip fractures occurring in the hospital. Am J Epidemiol 1994; 140: 830-8.
Morse JM, Tylko SJ, Dixon HA. Characteristics of the fall prone patient. Gerontologist 1987; 27: 516-22.
Passaro A, Volpato S, Romagnoni F et al. Benzodiazepenes with different half life and falling in a hospitalised population: The GIFA Study. J Clin Epidem 2000; 53: 1222-9.
Salgado R, Lord S, Packer J. Factors associated with falling in elderly hospital inpatients. Gerontology 1994; 40: 325-31.
Schmid NA. Reducing falls, a research based comprehensive fall prevention programme. Military Med 1990; 155: 202-7.
Sutton J, Standen P, Wallace W. Patient accidents in hospital: incidence, documentation and significance. Br J Clin Pract 1994;48: 63.
Simpson, J. et al., "Inpatient Falls: Defining the Problem and Identifying Possible Solutions. Part I: An Evidence-Based Review", The Neurohospitalist, 2013.
Predictive risk factors associated with stroke patient falls in acute care settings. Byers V, Arrington ME, Finstuen KJ Neurosci Nurs. Jun. 1990; 22(3):147-54.
Hospital falls: development of a predictive model for clinical practice. Hendrich A, Nyhuis A, Kippenbrock T, Soja ME Appl Nurs Res. Aug. 1995; 8(3):129-39.
Validation of the Hendrich II Fall Risk Model: a large concurrent case/control study of hospitalized patients. Hendrich AL, Bender PS, Nyhuis A Appl Nurs Res. Feb. 2003; 16(1):9-21.
Fall risk assessment: a prospective investigation of nurses' clinical judgement and risk assessment tools in predicting patient falls. Myers H, Nikoletti S Int J Nurs Pract. Jun. 2003; 9(3):158-65.
Predictors of falling in elderly hospital patients. Salgado RI, Lord SR, Ehrlich F, Janji N, Rahman A Arch Gerontol Geriatr. May-Jun. 2004; 38(3):213-9.
Ivziku D, Matarese M, Pedone C.Predictive validity of the Hendrich fall risk model II in an acute geriatric unit. Int J Nurs Stud. 2011;48(4):468-474.
Ackerman DB, Trousdale RT, Bieber P, Henely J, Pagnano MW, Berry DJ.Postoperative patient falls on an orthopedic inpatient unit. J Arthroplasty. 2010;25(1):10-14.

(56) References Cited

OTHER PUBLICATIONS

Cutillo-Schmitter TA, Rovner BW, Shmuely Y.Falls prevention study: a practical approach. J Healthc Risk Manag. 1996;16(4):56-68.

Evans D, Hodgkinson B, Lambert L, Wood J.Falls risk factors in the hospital setting: a systematic review. Int J Nurs Pract. 2001;7(1):38-45.

O'Hagan C, O'Connell B.The relationship between patient blood pathology values and patient falls in an acute-care setting: a retrospective analysis. Int J Nurs Pract. 2005;11(4):161-168.

Salameh F, Cassuto N, Oliven A. A simplified fall-risk assessment tool for patients hospitalized in medical wards. Isr Med Assoc J. 2008;10(2):125-129.

Chen YC, Chien SF, Chen LK. Risk factors associated with falls among Chinese hospital inpatients in Taiwan. Arch Gerontol Geriatr. 2009;48(2):132-136.

Frels C, Williams P, Narayanan S, Gariballa SE. Iatrogenic causes of falls in hospitalised elderly patients: a case-control study. Postgrad Med J. 2002;78(922):487-489.

Giles LC, Whitehead CH, Jeffers L, McErlean B, Thompson D, Crotty M. Falls in hospitalized patients: can nursing information systems data predict falls?Comput Inform Nurs. 2006;24(3):167-172.

Hitcho EB, Krauss MJ, Birge S, et al. Characteristics and circumstances of falls in a hospital setting: a prospective analysis. J Gen Intern Med. 2004;19(7):732-739.

Amador LF, Loera JA. Preventing postoperative falls in the older adult. J Am Coll Surg. 2007;204(3):447-453.

Härlein J, Halfens RJ, Dassen T, Lahmann NA.Falls in older hospital inpatients and the effect of cognitive impairment: a secondary analysis of prevalence studies. J Clin Nurs. 2011;20(1-2):175-183.

Oliver D, Hopper A, Seed P. Do hospital fall prevention programs work? A systematic review. J Am Geriatr Soc. 2000;48(12):1679-1689.

Oliver D, Daly F, Martin FC, McMurdo ME. Risk factors and risk assessment tools for falls in hospital in-patients: a systematic review. Age Ageing. 2004;33(2):122-130.

Papaioannou A, Parkinson W, Cook R, Ferko N, Coker E, Adachi JD. Prediction of falls using a risk assessment tool in the acute care setting. BMC Med. Jan. 2004;2:1.

Schmid AA, Wells CK, Concato J, et al. Prevalence, predictors, and outcomes of poststroke falls in acute hospital setting. J Rehabil Res Dev. 2010;47(6):553-562.

Using information technology to assist in redesign of a fall prevention program. Browne JA, Covington BG, Davila Y J Nurs Care Qual. Jul.-Sep, 2004; 19(3):218-25.

Accidental falls in hospital inpatients: evaluation of sensitivity and specificity of two risk assessment tools. Lovallo C, Rolandi S, Rossetti AM, Lusignani M J Adv Nurs. Mar. 2010; 66(3):690-6.

Using the Care Dependency Scale for fall risk screening. Mertens EI, Halfens RJ, Dassen T J Adv Nurs. Jun. 2007; 58(6):594-601.

Corsinovi L, Bo M, Ricauda Aimonino N, et al. Predictors of falls and hospitalization outcomes in elderly patients admitted to an acute geriatric unit. Arch Gerontol Geriatr. 2009 2009;49(1):142-145.

Grue EV, Ranhoff AH, Noro A, et al. Vision and hearing impairments and their associations with falling and loss of instrumental activities in daily living in acute hospitalized older persons in five Nordic hospitals. Scand J Caring Sci. 2009;23(4):635-643.

Heinze C, Halfens RJ, Dassen T.Falls in German in-patients and residents over 65 years of age. J Clin Nurs. 2007;16(3)495-501.

Jones WJ, Simpson JA, Pieroni RE.Preventing falls in hospitals. The roles of patient age and diagnostic status in predicting falls. Hosp Top. 1991;69(3):30-33.

Kerzman H, Chetrit A, Brin L, Toren O. Characteristics of falls in hospitalized patients. J Adv Nurs. 2004;47(2)223-229.

Nakai A, Akeda M, Kawabata I.Incidence and risk factors for inpatient falls in an academic acute-care hospital. J Nihon Med Sch. 2006;73(5):265-270.

Angalakuditi MV, Gomes J, Coley KC.Impact of drug use and comorbidities on in-hospital falls in patients with chronic kidney disease. Ann Pharmacother. 2007;41(10):1638-1643.

Capone LJ, Albert NM, Bena JF, Morrison SM.Characteristics of hospitalized cancer patients who fall. J Nurs Care Qual. 2010;25(3):216-223.

Chang CM, Chen MJ, Tsai CY, et al. Medical conditions and medications as risk factors of falls in the inpatient older people: a case-control study. Int J Geriatr Psychiatry. 2011;26(6):602-607.

"The incidence of falls in intensive care survivors", Patman, SM , Dennis, D , and Hill, K Australian critical care : official journal of the Confederation of Australian Critical Care Nurses (vol. 24 issue 3 pp. 167-174) Aug. 2011.

Rhalimi M, Helou R, Jaecker P. Medication use and increased risk of falls in hospitalized elderly patients: a retrospective, case-control study. Drugs Aging. 2009;26(10):847-852.

Shoff RI, Guillen MK, Rosenblatt LC, Walker K, Caudle CE, Kritchevsky SB. Restraint use, restraint orders, and the risk of falls in hospitalized patients. J Am Geriatr Soc. 2002;50(3):526-529.

Shuto H, Imakyure O, Matsumoto J, et al. Medication use as a risk factor for inpatient falls in an acute care hospital: a case-crossover study. Br J Clin Pharmacol. 2010;69(5):535-542.

McFarlane-Kolb H. Falls risk assessment, multitargeted interventions and the impact on hospital falls. Int J Nurs Pract. 2004;10(5):199-206.

Czernuszenko A, Czionkowska A. Risk factors for falls in stroke patients during inpatient rehabilitation. Clin Rehabil. 2009;23(2):176-188.

Jane McCurley, James Pittman, "A New Approach to Fall Prevention in Inpatient Care, Implementing Remote Audiovisual Monitoring of At-Risk Patients", http://psqh.com/november-december-2014/a-new-approach-to-fall-prevention-in-inpatient-c, 2014.

Leipzig R, Cumming R, Tinetti M. Drugs and falls in older people: a systematic review and meta-analysis: I/II. J Am Geriatr Soc 1999; 47: 30-50.

Harding, A.D. (2010). Observation assistants: Sitter effectiveness and industry measures. Nursing Economic$, 28(5), 330-336.

Degelau J, Belz M, Bungum L, Flavin PL, Harper C, Leys K, Lundquist L, Webb B, Institute for Clinical Systems Improvement (ICSI). Prevention of falls (acute care). Health care protocol. Bloomington (MN): Institute for Clinical Systems Improvement (ICSI); Apr. 2012. 43.

Jaworowski, S., Raveh, D., Lobel, E., Fuer, A., Gropp, C., & Mergui, J. (2008). Constant observation in the general hospital: A review. Israel Journal of Psychiatry and Related Sciences, 45(4), 278-284.

Feil, M., & Wallace, S. (2014). The use of patient sitters to reduce falls: Best practices. Pennsylvania Patient Safety Authority. 11(1), 8-14.

Tzeng, H. M., Yin, C. Y., & Grunawalt, J. (2008). Effective assessment of use of sitters by nurses in inpatient care settings. Journal of Advanced Nursing. 64(2), 176-184.

Richman, C. et al., "Patient Sitter Use Within Hospitals: A Cross-Sectional Study", Final Report to the International Healthcare Security and Safety Foundation, Dec. 2014.

Blumenfield, M., Milazzo, J., & Orlowski, B. (2000). Constant observation in the general hospital. Psycho somatics, 41, 289-293.

Salamon, L., & Lennon, M. (2003). Decreasing companion usage without negatively affecting patient outcomes: A performance improvement projec. Medsurg Nursing, 12(4), 230-236.

Worley, L.L.M., Kunkel, E.J.S., Gitlin, D.F., Menefee, L.A., & Conway, G. (2000). Constant observation practices in the general hospital setting. Psychosomatics, 41, 301-310.

Lamban, R.M., Ramchandani, D., & Schindler, B.A. (1996). Constant observation in a medical-surgical setting. The role of consultation-liaison psychiatry. Psychosoma tics, 37(4), 368-373.

Moore, P., Berman, K., Knight, M., & Devine, J. (1995). Constant observation: Implications for nursing practice.Journal of Psychosocial Nursing, 33(3), 46-50.

O'Dowd, M.A., Freedman, J.B., Bernstein, G., Ricco, P., & McKegney, F.P. (1995). Reduction in use of constant observation in the general hospital and cost savings as a result of quality improvement monitoring.Psychosomatics, 36, 189-190.

(56) References Cited

OTHER PUBLICATIONS

Frengley JD, Mion LC. Physical restraints in the acute care setting. Issues and future direction. Clin Geriatr Med 1998; 14: 727-42.
Parker K, Miles S. Deaths caused by bedrails. J Am Geriatr Soc 1997; 45: 797-802.
Medical Devices Agency Website—safety warnings.www.medical-devices.gov.uk.
Guidelines for the prevention of falls in older persons. American Geriatrics Society, British Geriatrics Society and American Association of Orhopaedic Surgeons Panel on Falls Prevention. J Am Geriatr Soc 2001; 49: 664-72.
Ejaz F, Jones J, Rose M. Falls among nursing home residents: an examination of incident reports before and after restraint reduction programs. JAm Geriatr Soc 1994; 42: 960-4.
Maciorowski LF, Munro B. A review of the patient fall literature. J Nurs Qual Assur 1988; 3: 18-27.
Ballinger B, Ramsay A. Accidents and drug treatment in a psychiatric hospital. Br J Pyschiatr 1976; 126: 462-3.
Mahoney J. Immobility and falls. Clin Geriatr Med 1998; 14: 700.
Gillon R. Medical ethics: four principles plus attention to scope. Br Med J 1994; 309: 184-8.19.
Jennifer R. Simpson, Laura D. Rosenthal, Ethan U. Cumbler, and David J. Likosky, "Inpatient Falls: Defining the Problem and Identifying Possible Solutions. Part I: An Evidence-Based Review", The Neurohospitalist 3(3) 135-143.
Counsel and Care. The Right to take risks. London: Counsel and Care, 1993.
AvaSure, www.avasure.com, Accessed Feb. 2019.
R. Su, I. Kirenko, Design and Validation of Algorithms for Camera-based Patient Activity Monitoring, Technical Note PR-TN-2014/00435.
Agency for Healthcare Research Quality, "Hospital Resources", https://www.ahrq.gov/professionals/systems/hospital/index.html, Accessed Feb. 2019.
Patient Safety Authority, http://patientsafety.pa.gov/, Accessed Feb. 2019.
ECRI Institute, https://www.ecri.org/, Accessed Feb. 2019.
Joint Commerce Resources, https://www.jcrinc.com/, Accessed Feb. 2019.
Minnesota Hospital Association, https://www.mnhospitals.org/quality-patient-safety/current-safety-quality-initiatives/falls, Accessed Feb. 2019.
US Department of Veterans Affairs, https://www.visn8.va.gov/patientsafetycenter/, Accessed Feb. 2014.
"A New Approach to Fall Prevention in Inpatient Care", Patient Safety and Quality Healthcare, https://www.psqh.com/analysis/a-new-approach-to-fall-prevention-in-inpatient-care/, Accessed Feb. 2019.
"Better Care Victoria", https://www2.health.vic.gov.au/hospitals-and-health-services/quality-safety-service/better-care-victoria, Accessed Feb. 2019.
Monash University Accident Research Centre, https://www.monash.edu/muarc, Accessed Feb. 2019.
Morse JM. Enhancing the safety of hospitalization by reducing patient falls. Am J Infect Control 2002;30(6):376-80.
Rigby K, Clark R, Runciman W. Adverse events in health care: Setting priorities based on economic evaluation. Journal of Quality Clinical Practice 1999;19:7-12.
"Preventing Falls in Hospitals", Agency for Healthcare Research Quality, https://www.ahrq.gov/professionals/systems/hospital/fallpxtoolkit/fallpxtk3.html, Accessed Feb. 2019.

* cited by examiner

DEVICE, SYSTEM AND METHOD FOR PATIENT MONITORING TO PREDICT AND PREVENT BED FALLS

CROSS-REFERENCE TO PRIOR APPLICATIONS

This application is the U.S. National Phase application under 35 U.S.C. § 371 of International Application No. PCT/EP2017/071007, filed on 21 Aug. 2016, which claims the benefit of European Patent Application No. 16185483.1, filed on 24 Aug. 2016. These applications are hereby incorporated by reference herein.

FIELD OF THE INVENTION

The present invention relates to a device for monitoring individuals, especially patients in a hospital or under homecare, the device being adapted to allow prediction of an eminent fall of the person out of bed. The device emits an alarm when a number of connected risk factors exceed a defined threshold. The present invention further relates to a system incorporating the aforementioned device and a method of monitoring individuals to predict bed falls.

BACKGROUND OF THE INVENTION

Falls are the most common adverse event reported in hospitals and are a leading cause of hospital-acquired injury, and frequently prolong or complicate hospital stays. Reviews of observational studies in acute care hospitals show that fall rates range from 1.3 to 8.9 falls/1,000 patient days and that higher rates occur in units that focus on eldercare, neurology and rehabilitation. In spite of extensive research on falls risk factors and the development of a number of falls risk instruments, protocols are applied inconsistently, and risk factor directed interventions are far from standardized.

Although falls can occur at all ages, they are known to lead to significant injury in older people or those from high falls risk populations when compounded by an acute health problem requiring hospitalization, or for those requiring admission to residential care settings.

In addition, other observational studies show that 60-70% of all falls in hospital occur from the bed or bedside chair, that more than 80% of falls are unwitnessed and that about 50% occur in patients who fall repeatedly.

Given the high impact of fall incidents on patients' health and quality of life as well as costs of care, finding scalable and cost efficient solutions for patient monitoring and fall prevention to reduce the number of bed falls incidents becomes of utmost importance.

The current state of art includes solutions such as sitter services as means for bed fall incidents prevention, bed rails as means for bed fall incidents prevention and certain automatic solutions for patient monitoring.

Sitter service is difficult to implement, not scalable and not cost efficient. Towards its implementation hospitals typically must choose between employing sitters from outside the hospital staff which is financially taxing due to the service high costs or assigning sitter duties to their own hospital staff, which increases significantly the responsibilities and workload of the staff, typically already overburdened due to staff shortages. In addition assigning sitter tasks (that do not require medical training) to qualified staff prevents appropriate use of personnel qualifications and skills.

In that sense sitter services do not present a favorable outlook when it comes to implementing a reliable, scalable and cost efficient prevention strategy for inpatient bed fall incidents.

Bed rails as a single prevention strategy do not seem to guarantee the prevention of bed fall incidents. 50-90% of falls from bed in hospital occur despite bedrails being applied, showing limited success in preventing falls in general. In addition bedrail use may also be associated with worsening of agitation, fear and delirium. "Chemical" restraint e.g. in the form of neuroleptic use despite the misguided intention to prevent falls by its use is associated with increased fall rates. Moreover, restraint or bed rail use can lead to muscle wasting, infection or pressure sores from immobility, and deconditioning. Finally there is an ethical component to be considered when it comes to restricting patient moving ability.

Technology based products have been used in an attempt replace sitter service but may also have innate drawbacks. Some systems do not provide any intelligence to support the so-called "eSitter" in monitoring patients, which limits the number of patients monitored in parallel. As the scalability of such solutions is limited, up-scaling requires additional devices and remote monitoring stations. No intelligence implemented to determine automatically the fall risk in real time raises concerns and puts in question the feasibility of fall incidents prevention. Fall risk assessed is based on input obtained upon initial and ongoing patient contact by hospital staff but is not updated based on continuous automatic observation of patient in real time. As updates of the fall risk are based on interviews with the patient at admission and during hospitalization, these updates are liable to inaccuracy and significant delays, raising further concerns.

Other systems implement a technical approach where whenever a partial bed edge crossing happens (by the blanket or by patient arm) without an actual patient bed-exit, the system triggers an alarm. This leads to a high rate of false alarms.

In addition regarding effective preventive interventions, these technologies focus very much on monitoring and alarms but no attention is given to understanding the most optimal intervention that should be provided given a particular patient profile at a certain time. Furthermore, if medical staff should intervene, these systems do not provide support in determining the actual persons who should be notified, in order to optimize staff resources. Finally all alerts are issued only when the risk of falling is very high and the incident occurrence is imminent, at which point the chance of providing an effective intervention that actually prevents the fall is decreased.

WO 2010/105203 A2 refers to a method and apparatus for elder care monitoring. The apparatus comprises an adherent device configured to adhere to the skin of the elder and measure data with two or more sensors to measure patient data. The patient data can be transmitted with wireless communication circuitry, such that the patient can be monitored and subtle changes in physiology can be detected such that appropriate action may be taken. The patient data from two or more sensors can be combined to determine the status of the patient. For example, hydration data can be combined with activity data to determine a status of the elder person, and transmit a notification to friend to monitor compliance with medication and a notification to a physician to diagnose the mental health of the elder.

SUMMARY OF THE INVENTION

It is an object of the present invention to provide a device, a system and a method for monitoring of patients which not only monitors the movement patterns and the vital signs of the patient but also assesses the data and evaluates a risk score which on the one hand allows reliable prediction and on the other hand minimizes false alarms, thus allowing efficient but attentive care for the patients.

In a first aspect of the present invention a device for detection of a vital signs related risk score for a bed fall risk of an individual is presented that comprises a first port for obtaining vital signs data related to a vital sign of the individual and a vital signs processing unit for obtaining and processing the vital signs data to generate a vital signs related risk score indicating the bed fall risk of the individual by detecting at least one risk factor from the vital signs data and computing the vital signs risk score from the at least one risk factor.

In a further aspect of the present invention a system for determination of a bed fall risk of an individual is presented that comprises at least one vital signs sensor for acquiring vital signs sensor data related to a vital sign of the individual and a device for determination of a bed fall risk of an individual based on the acquired vital signs sensor data.

In another aspect of the invention a method for determination of a bed fall risk of an individual is presented, the method comprising the steps of obtaining sensor data related to a vital sign of an individual and processing the vital signs data to generate a vital signs related risk score indicating the bed fall risk of the individual by detecting at least one risk factor from the vital signs data and computing the vital signs risk score from the at least one risk factor.

In yet a further aspect of the invention a computer program comprising program code means for causing a computer to carry out the steps of the method when said computer program is carried out on a computer is presented.

The inventive device, system, method and computer program for determination of a bed fall risk differ to the state of art described above in that the vital signs detected by the device are base for an assessment of risk factors connected to the respective vital signs. By this assessment not the vital sign as such which might be misleading is used directly for calculation of the risk score. Instead, several risk factors are determined and can be observed and their development is then be used to evaluate the individuals' risk for a bed fall. This implies a higher accuracy and less false alarms.

Preferred embodiments of the invention are defined in the dependent claims. It shall be understood that the claimed method has similar and/or identical preferred embodiments as the claimed device and as defined in the dependent claims.

Preferably the device further comprises an evaluation unit configured to assign a reliability value to said vital signs data and/or said vital signs related risk score and to evaluate a variable risk score of the individual from the reliability value and the vital signs risk score. By way of this, an assessment of the reliability of the signal is possible. If the signal is not reliable for a bed fall prediction, the system can give out an alert and use other sources of information.

According to a preferred embodiment the risk factor is a psychogenic status, in particular tension or stress, anxiety, restlessness, agitation, and/or a posture, in particular raising of the torso, leaning over the bed edge, reaching out of bed. These risk factors are easy to monitor without need of extensive technical equipment.

Advantageously the vital signs data comprise accelerometer data, heart rate monitoring data, heart rate variability monitoring data, respiration monitoring data. These data can be monitored by well-established devices present in any care environment.

The processing unit is preferably configured to obtain accelerometer data in channels corresponding to spatial directions x, y, z, wherein the x direction is oriented along a length of a bed where the individual is located in, the z direction is oriented along a width of the bed, and the y direction is oriented along an axis perpendicular to a plane of the bed spanned by the x and z directions. By way of this, the posture of the individual can be easily detected and the position relative to the bed plan can be used to predict an imminent bed fall incident.

According to another advantageous embodiment the processing unit is configured to detect tension or stress and anxiety of the individual located in the bed by observing heart rate monitoring data, respiration monitoring data, heart rate variability monitoring data and accelerometer data in a predetermined time window, wherein the heart rate monitoring data, respiration monitoring data, heart rate variability monitoring data surpass predetermined values and the accelerometer data are below a predetermined value in all spatial directions x, y, z. Definition of thresholds which are surpassed or not further helps to detail the behavior of the individual in context with the vital signs data.

Preferably the processing unit is configured to detect the posture of the individual located in the bed by detecting, counting and analyzing the accelerometer data in the channels according to the spatial directions x, y, z. Accelerometer sensors are easy to handle and small enough to be arranged on the individual without disturbing the person under care.

Advantageously the processing unit is configured to detect restlessness or agitation of the individual located in the bed by observing heart rate monitoring data, respiration monitoring data, heart rate variability monitoring data and accelerometer data in a predetermined time window, wherein the heart rate monitoring data, respiration monitoring data, heart rate variability monitoring data surpass predetermined values and the accelerometer data of at least one channel corresponding to the spatial directions x, y, z surpass a predetermined threshold. In case that the predetermined thresholds are all surpassed the imminent danger of a bed fall can be reliably assessed and the respective care program can be initiated without delay.

According to yet another advantageous embodiment the accelerometer data of the channels corresponding to the x and z direction surpass the predetermined threshold and the accelerometer data of the y direction is below the predetermined threshold for the risk factor of restlessness.

According to an alternative preferred embodiment the accelerometer data of the channels corresponding to the x and y direction surpass the predetermined threshold and the accelerometer data of the z direction is below the predetermined threshold for the risk factor of agitation. By separating the accelerometer movements in x, y and z direction any combination of the three spatial components can be combined to describe a different movement pattern and assign this pattern to a pathologic condition of the individual. Thus, the different movements can be used to better determine the associated risk factors and to predict an imminent bed fall more precisely.

The vital signs processing unit is advantageously configured to determine the vital signs risk score and/or the reliability value at discrete intervals or continually. The mode can be chosen in dependency of the behavior of the individual. If e.g. sedation has been administered and the person under care is quite still in position, a longer interval for the measurement of the vital signs can be chosen. This produces less data. If the individual is moving a lot, the determination of the vital signs and the related risk score and reliability values can be shifted to a continuous mode to make sure to keep track of the values.

According to an another advantageous embodiment the vital signs sensor is at least one of an accelerometer, a photoplethysmography sensor, a heart rate monitor, a blood pressure monitor, an SpO2 sensor, a respiration monitor. The sensors mentioned before are well-established with regard to use and maintenance and do not require specific knowledge of the medical staff. Many of the sensors are also available in a fully automatized version, thus allowing easy use without the need of monitoring by medical staff.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE EMBODIMENTS

Figure 1:
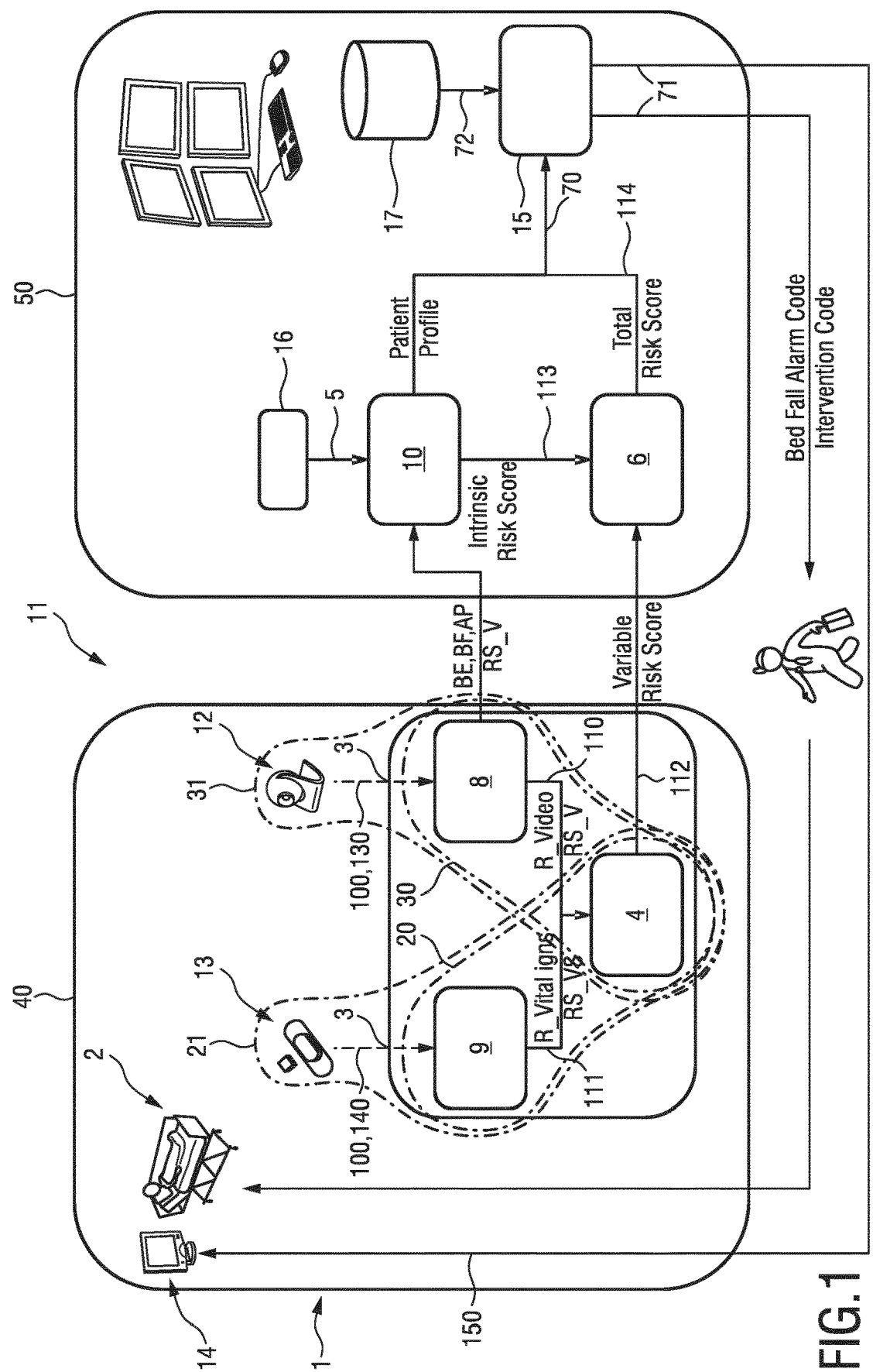
FIG. 1 shows a schematic overview over an inventive device and system for monitoring of patients and for predicting and preventing bed falls.

In FIG. 1, an overview of a preferred embodiment of the invention is diagrammatically shown. The embodiment comprises a device 1 for monitoring an individual 2. The individual 2 can be especially a patient in a hospital bed. In the following, the individual 2 thus will be addressed as patient 2, but the individual 2 could also be a resident of a nursing home, an occupant in a psychiatric ward, an individual 2 under home care or the like. The principle at the basis of the device 1 is that the bed fall risk associated with patients 2 under monitoring is determined both by unmodifiable risk factors such as age, certain debilitating (permanent) conditions, physical impairments etc. of the patient 2, as well as the psychologic make-up (regarding level of compliance/adherence to medical guidelines in the hospital) and modifiable risk factors such as restlessness, level of confusion, level of anxiety, type and speed of movement (e.g. erratic movements) of the patient 2 while occupying the bed.

The device 1 ensures that the calculation of a risk score associated with each patient 2 is based on an assessment of all risk factors above (unmodifiable and modifiable), and that intervention strategies implemented are tailored to each patient 2 to ensure full effectiveness of the solution by preventing bed fall incidents as well as optimization of medical staff resources by only involving the medical personnel when needed, and then involving the staff most accessible and/or available to accomplish the intervention.

The device 1 of the embodiment of FIG. 1 connects via first ports 3 to sensors 12 and 13 being located in a patient room 40 where the patient 2 is situated. The embodiment especially provides the sensor 12 in form of a video camera 12 or another suitable device for monitoring movement of the patient 2 and the sensor 13 in form of a vital sign sensor 13. The vital sign sensor 13 can in particular be a photoplethysmography sensor, a heart rate monitor, a blood pressure monitor, an SpO2 sensor and/or a respiration monitor which all are suitable to evaluate vital signs and simultaneously allow conclusions to be drawn about stress, anxiety, agitation and the like. The vital sign sensor 13 can be arranged on the patient's body or in a remote location, especially in case when a PPG sensor is used. The sensors 12, 13 taking input in real time either continuously or at discrete intervals thus provide a certain redundancy for the monitoring, allowing an accurate and failsafe prediction of incidents. In case one of the sensors 12, 13 is out of order, the other still can provide data.

Sensor data 100 collected by the sensors 12, 13, i.e. video data 130 and vital signs data 140, are transferred to a video processing unit 8 and a vital signs processing unit 9, respectively. The processing units 8, 9 are configured to detect in real time risk factors by analyzing the video data 130 and the vital signs data 140 and to calculate a risk score 110, 111 for each data set based on the risk factors detected. The video processing unit 8 and the vital sign processing unit 9 and their functions will be described later in more detail with reference to FIGS. 2 to 15.

The device 1 further contains an evaluation unit 4 for determining quality information indicating the quality of the sensor data 100. Thus the reliability of the video data 130 and the vital signs data 140 are assessed and weighted. The evaluation unit 4 obtains the risk scores 110, 111 from the respective processing units 8, 9, determines a reliability value for the respective data 130, 140 and calculates a variable risk score 112 therefrom as described later in more detail. The vital signs processing unit 9 in connection with the evaluation unit 4 may be addressed as vital signs risk score detection device 20, whereas the video processing unit 8 in connection to the evaluation unit 4 may be addressed as video data risk score detection device 30. The respective video sensor 12 and vital sign sensor 13 in connection with the respective devices 30 and 20 may be addressed as systems 31 and 21.

The evaluation unit 4 uses the risk factors 110 and 111 (defined above) as well as sensor reliability indicators (as described in detail further below) in order to calculate in real-time an overall patient variable risk score 112 for bed fall incidents. The variable risk score 112 is transmitted to a calculation unit 6 for further processing. Especially, the variable risk score 112 can be transmitted from the patient room 40 to a remote workstation room 50 via a network communication protocol.

The sensor reliability indicates the level of confidence associated with each sensor depending on environmental and connectivity factors as described in detail with reference to the functionality of the video and vital signs processing units 8, 9 further below.

As such the variable risk score 112 is defined to be a composite of the R_Video and R_VitalSigns (defined above) where the sensors reliability indicators (SR_V and SR_VS) act as weighting factors. As an example, in a potential implementation if both SR_V and SR_VS are 0, then the Variable Risk Score is set to −1, indicating the system is not able to calculate the Variable Risk Score due to unreliable input. In all other cases:

$$\text{Variable Risk Score} = (SR\_V * R\_\text{Video} + SR\_VS * R\_\text{VitalSigns})/(SR\_V + SR\_VS)$$

The formula above implies that whenever the video signal is not reliable, the variable risk score 112 is in effect equal to R_VitalSigns. Conversely, if the vital signs signal is not reliable, the variable risk score 112 is in effect equal to R_Video. If both signals are viable then the variable risk score 112 is an average of the two risk scores 110 and 111 above. Expressed in pseudocode:
if (SR_V=0 AND SR_VS=0) then variable risk score=−1 else variable risk score=(SR_V*R_Video+
    SR_VS*R_VitalSigns)/(SR_V+SR_VS).

The components previously described are arranged in the vicinity of the patient 2. The following components however advantageously are arranged in the remote workstation room 50.

A classification unit 10 classifies patients 2 based on their clinical and psychological profiles and provides an intrinsic risk score 113 based on the patient profile. The patient profile in the current embodiment is obtained from a database 16 via a second port 5. The patient profile includes any information available about the patient 2, starting with age and gender and further containing the current diagnosis, respective medication, the allover condition of the patient, the medical history and the bed fall history and so on. The patient profile thus is a major source for assessment of the bed fall risk of a patient 2.

The personal data 120 provide unmodifiable risk factors constituting the clinical and psychological profiles, and provide the intrinsic risk score 113 therefrom.

Unmodifiable risk factors may be patient age (older patients are at higher risk of developing cognitive impairments and therefore would have an increased bed fall risk), patient gender (male patients appear to be at higher risk for falling incidents, possibly due to higher reluctance to receive assistance when leaving the bed), (neurologic) condition (dementia (e.g. Alzheimer) patients and patients with Parkinson's Disease are known to run a higher risk of falling out of bed due to being more prone to spatial disorientation, agitation episodes, and acting out their dreams due to sleeping disorders. Having a neurological disease would correspond to increased bed fall risk level as opposed to not having these diseases), current or previous symptoms (registered/observed occurrences of hallucination/sleeping disorders will increase the bed fall risk levels, (cognitive, visual) disabilities (visually impaired patients will run a higher risk of not estimating well distances, be spatially unaware contributing to an increased bed fall risk level), medications (large number of prescription medications, or patients taking medicines that could cause sedation, confusion, impaired balance, or orthostatic blood pressure changes are at higher risk for falls, bed falling history (consistent history of bed falling episodes will increase the likelihood of a subsequent repeated event as opposed to sporadic (or no previous history) of such events), and psychologic profile—compliance/adherence level (patients with lower levels of compliance/adherence to medical guidelines during their hospitalization (e.g. do not leave the bed un-attended) are at higher risk for falling while attempting to exit the bed than otherwise).

All unmodifiable factors mentioned above (except bed fall history and psychological profile) are determined by the classification unit 10 from the patient electronic health record 16 as shown in FIG. 1.

Patient bed fall history is assessed via a simple question regarding the number of falls the patient experienced so far. Patient psychological profile (regarding the patient level of compliance/adherence to medical guidelines in the hospital) is determined by means of a questionnaire test at hospitalization as a way of determining a baseline. This profile is updated based on further learning regarding the patient level of compliance/adherence with medical advice to not leave the bed un-attended, during the hospital stay.

The intrinsic risk score 113 is based on assessing the unmodifiable risk factors mentioned above, where the intrinsic risk score is increased by a parameter $xi$ ($i=1 \ldots 8$)—associated with each risk factor. This would imply the following tests and associated computations:

If Patient Age>65 then

Intrinsic Risk Score=Intrinsic Risk Score$\otimes x1$

If Patient Gender=male then

Intrinsic Risk Score=Intrinsic Risk Score$\otimes x2$

If Patient (Neurologic) condition=yes then

Intrinsic Risk Score=Intrinsic Risk Score$\otimes x3$

If Patient disabilities (visual or motoric)=yes then

Intrinsic Risk Score=Intrinsic Risk Score$\otimes x4$

If Patient medication (causing sedation etc.)=yes then

Intrinsic Risk Score=Intrinsic Risk Score$\otimes x5$

If Patient symptoms=yes then

Intrinsic Risk Score=Intrinsic Risk Score$\otimes x6$

If Patient having a bed falling history=yes then

Intrinsic Risk Score=Intrinsic Risk Score$\otimes x7$

If Patient level of adherence=low then

Intrinsic Risk Score=Intrinsic Risk Score$\otimes x8$ wherein in a simple example "$\otimes$" could stand for a simple sum.

At system initialization parameters x1 to x8 can be initialized based on values indicated by literature studies, while over time, the system adjusts the parameters values by learning the influence of each risk factor above on a bed fall occurrence, for the specific population at hand. This is done by executing correlation analyses and applying regression techniques after each bed fall incident to understand the impact of each risk factor on the likelihood of a bed fall event and to update the values of the parameters above. All risk factors indicated above are known from medical literature to have a causative relevance to the occurrence of fall incidents. The question remains how much of a causative relevance each risk factor has for each patient (given their certain patient profile). Parameters x1 to x8 quantify the causative relevance of their associated risk factors, this making their determination necessary. Determination is done by evaluation of the level of correlation between the presence of their (associated) risk factors and the occurrence of a fall incident. That is, the higher the number of times the occurrence of a risk factor precedes the occurrence of a fall incident, the higher the likelihood that the risk factor has a higher causative relevance to the occurrence of a fall incident for a patient with a certain profile. If a risk factor causes a fall incident, then it has a predictive power as well. Correlation quantifies the degree to which two variables are related—in this case a risk factor and a fall occurrence. Computing a correlation coefficient (r) indicates how much one variable tends to change when the other one does. For that reason in an embodiment, parameters x1 to x8 could be represented by the correlation coefficients (or a factor of these) for example. As time passes the systems becomes increasingly accurate in determining this intrinsic risk. If no bed fall incident occurs no parameter adjustment is needed.

Further, a calculation unit 6 is provided which obtains the variable risk score 112 from the evaluation unit 4 and the intrinsic risk score 113 from the classification unit 10 and therefrom calculates a total risk score 114. The latter is together with the patient profile obtained from the database 16 the input to an intervention unit 15 which provides strategies for the prevention of an imminent bed fall of a patient 2 based on the patient's clinical and psychological profile and the total risk score 114. The total risk score 114 is a composite of the intrinsic risk score 113 and the variable risk score 112 values:

Total Risk Score=Intrinsic Risk Score⊗Variable Risk Score

In a potential implementation the formula could express a weighted sum or weighted average of the two risk scores 112 and 113 above where the weights can be updated based on continuous system learning from the data of the population monitored expressing the level of impact of modifiable and unmodifiable risk factors.

The device 1 according to the preferred embodiment may further correspond to additional components like a feedback unit 14 which is located in the vicinity of the patient 2 and which can directly address the patient 2 in case the device 1 detects an imminent bed fall. Generally, the device 1 preferably has a configuration which provides as little components as possible in the patient room 40 and respectively the remote workstation room 50 where the other components are located. This configuration allows monitoring of a number of patients 2 in various locations without the necessity of a whole monitoring system for each patient 2.

According to the preferred embodiment of FIG. 1, in the patient room 40 only the following components are installed: the video camera 12, the vital signs sensor 13, the respective processing units 8, 9 and the evaluation unit 4. Alternatively, it would also be possible to arrange the processing units 8, 9 and the evaluation unit 4 in the remote workstation room 50 and to transmit the data 130, 140 e.g. by a wireless network thereto. Since nowadays modern video cameras 12 and vital signs sensors 13 are small components which can already be combined with their respective processing units 8, 9, these components can however be arranged unobtrusively in the patient room 40. Arrangement of the evaluation unit 4 in the vicinity of the processing units 8, 9 allows easier data administration since the individual sensor data 100 of each patient can be unambiguously assigned to the respective patient 2 and for example stored in a data storage (not shown) until they are requested from the calculation unit 6.

Further, the feedback unit 14 is arranged in the patient room 40. The feedback unit 14 can for example be a TV display equipped with a microphone which is normally provided anyway in each patient room 40 in a hospital for entertainment of the patients 2 and which can be used by the intervention unit 15 to communicate with the patient 2. Alternatively, the feedback unit 14 can be an additional, separate unit which can be part of a monitoring system which is rather used by the medical staff. In this case, the feedback unit 14 can also serve as a source of information for the staff entering the room in case there was an alert about an imminent bed fall.

In the following, the functionality of the video camera 12 and the respective processing unit 8 is described in more detail with reference to FIGS. 2 to 10. For the sake of simplicity, in the following the video camera 12 and the assigned processing unit 8 are termed as "video component", referring to the components with the reference numbers 12 and 8.

As mentioned above, the video component implements two main functionalities: on the one hand, the reliability of the video data 130 is assessed, on the other hand, detection of the presence of risk factors in real time is carried out, based on which a video data risk score 110 indicating the likelihood of a bed fall incident in view of the parameters detected by the video camera 12 is calculated. This functionality is executed only if the reliability of the video data 130 mentioned above is determined to be sufficient.

Assessment of the reliability of the video data 130 can for example be done by use of a variable to express video sensor reliability (SR_V). SR_V is set on 1 when the sensor reliability is assessed to be sufficient and 0 otherwise.

The assessment is primarily based on illumination levels, an estimation of the contrast variations of the moving objects in the scene and the signal to noise ratio of the camera and consequently also of the video data 130. Signal in this application is the minimal contrast change in a scene as result of a movement of an object in the scene. In that sense whenever illumination levels or the signal to noise ratio of the video data 130 are below a threshold (e.g. 6 lux, 3 dB signal to noise ratio), the sensor signal is determined to be not reliable and SR_V is set on 0. If both illumination and signal to noise ratio are above the threshold, SR_V is set on 1. The threshold depends on the camera type and quality used and must be set as such at initialization. This signal reliability assessment can be done either punctually with a certain frequency and/or during predetermined intervals or alternatively continually to check if the value of SR_V needs to be changed.

Detection of the risk factors and calculation of the video data risk score 110 is only done if the reliability value SR_V is found to be 1. For as long as the video data 130 are considered to be reliable, the video processing unit 8 processes the video data 130 and detects in real-time a number of risk factors which mainly refer to the patient's body posture and the position occupied in bed. Examples are: the patient's torso is up from a supine position, the patient 2 is restless, turns and tosses or the patient 2 is near the bed edge.

In addition the video component is able to detect events like intentional and unintentional bed exits of the patient 2. If the patient 2 exits the bed intentionally, a bed exit indicator will be set to 1 (BE=1) while otherwise it is set to 0. If the patient 2 has unintentionally fallen out of bed, a bed fall exit indicator will be set to 1 (BF=1) while otherwise it is set to 0. In case an additional person is present in room, an additional person indicator is set to 1 (AP=1) while otherwise it is set to 0.

Detecting the modifiable risk factors above allows calculating a video data risk score 110 for a bed fall incident based on the video data 130. If the camera is not reliable (SR_V=0) the processing unit 8 does not process the signal at all and the video data risk score 110 is set to −1 to indicate that the risk has not been assessed due to signal unreliability. If the video signal is found not to be reliable, then the system will react based on the risk score from the vital signs sensor 13 and vice-versa. If none of the signals are reliable then the device 1 sends a message to the intervention unit 15 that real-time monitoring is not possible and that a technical team needs to attend the patient room 40 to address issues and restore signal quality. According to a preferred embodiment, the device 1 can self-diagnose and write a log with the cause of the signal unreliability. In case of the vital signs signals this could e.g. be network bandwidth not sufficient, insufficient throughput, etc. In case of the video signal in-adequate illumination conditions etc. can be the cause of signal unreliability. The log can even provide statistics on the most present cause, location/patient room 40 most affected, etc. The log will then be used by the technical team to solve the issues.

The output of the video data processing unit 8 comprises the SR_V signal reliability indicator and the video data risk score 110. These data are delivered to the evaluation unit 4.

Besides, the video data processing unit 8 provides data for retrieval by the classification unit 10 to help learn the patient compliance levels, e.g. to not leave the bed unattended. The data handed over to the classification unit 10 are the SR_V signal reliability indicator, the BE and BF codes for detected intentional bed exit and unintentional bed fall events and the additional person indicator AP.

Figure 2:
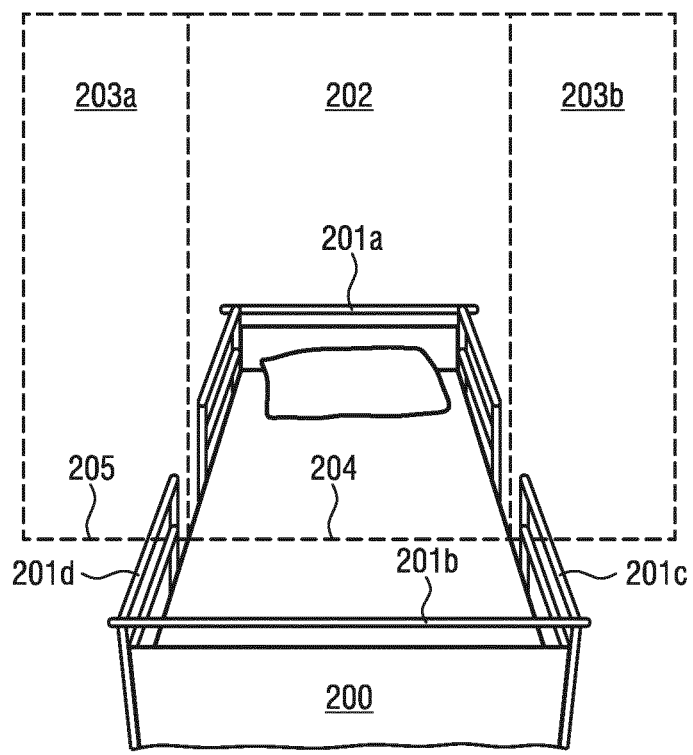
FIG. 2 shows a schematic view of the bed frame covered by a video component.

In the following, the algorithms for detection of the risk factors mentioned above are described. Reference is taken to FIG. 2 first.

In FIG. 2, a very schematic bed 200 for a patient 2 (not shown in FIG. 2) is illustrated.

The inventive device 1 for bed fall prediction assumes (x, y) coordinates of points indicating the bed space, e.g. the four bed edges 201*a*, 201*b*, 201*c* and 201*d*, in the frame covered by the video camera 12 to be known. The bed edges 201*a*, 201*b*, 201*c* and 201*d* can be indicated manually e.g. by drawing them in a visual editor which acts as an input device (not shown) or they could be detected automatically.

Based on the coordinates of the bed edges 201*a*, 201*b*, 201*c* and 201*d*, the algorithm executes the following steps:

1. Defines a first region of interest 202 and a second region of interest 203 which splits in two parts 203*a* and 203*b* arranged adjacent to the first region of interest 202 and adjacent of bed edges 201*c* and 201*d*, used later in detecting parameters;

2. Determines the valid motion trajectories within the second region of interest 203*a* and 203*b*, with valid trajectories being defined by a certain length and maximum variance determined based on learning;

3. Clusters valid motion trajectories to identify moving entities based on direction, slope, position and length over a number of image frames (currently 15 image frames—this threshold needs to be learned and adapted according to movement behavior in the scene, such as speed);

4. Determines the center of gravity motion of each entity by calculating the median of the x, y coordinates of the end point of all valid motion trajectories belonging to the entity;

5. Determines reference centers of motion gravity: the right-most center of motion gravity 401, this being the gravity center with the largest x coordinate of all gravity centers, the left-most center of motion gravity 400, this being the gravity center with the lowest x coordinate of all gravity centers, the highest center of motion gravity 402, this being the gravity center with the largest y coordinate of all gravity centers, and the global center of motion gravity, this being calculated based on the median of the x coordinate of the end point of all valid trajectories in the scene over all entities.

Trajectories are defined as trajectories of movement of objects in a video scene which are calculated based on changes in contrast of specific points in the scene. Those points are points which are indicated as possible starting trajectory points. The contrast variability of a point in the scene determines whether that point becomes a starting trajectory point. Starting by a candidate starting trajectory point the gradient in x- and y-direction in the image is calculated giving a direction of movement from that starting point. In this way the next trajectory point is determined. A trajectory is formed during a given number of video frames (e.g. 15 frames). When a trajectory has been formed during that number of frames a check is performed to accept or reject the trajectory as a valid trajectory. The validity of a trajectory can be done based on typical characteristics of a logical movement of an object. For instance the length of the trajectory, the curvature of the trajectory, the variation of the trajectory points etc. can be used as quality indicators for the acceptance of a trajectory.

An entity hereinafter is defined as a set of trajectories or a set of moving points in a scene with common characteristics. Clustering algorithms, i.e. the well-known k-means clustering can be used to cluster trajectories or moving points based on for instance color, length of trajectory, slope of trajectory, histogram of a trajectory points etc. It is to be noted here that a trajectory is calculated e.g. 15 frames long, but its length depends on the speed of the corresponding moving object. By clustering trajectories or moving points in the scene body parts of the patient but also other moving parts like bed sheets are identified as such due to their common characteristics.

The center of gravity values are based on the video information. Actually the gravity values are a different and simpler algorithm to cluster moving points and/or trajectories. The median value of the x-coordinates of all the moving points or starting points of trajectories in a region of interest 202, 203 (described below) in the scene is calculated to come with the x-coordinate value of the center of gravity 400, 401. Comparable, the median value of the y-coordinates of all the moving points or starting points of trajectories in a region of interest 202, 203 in the scene is calculated to come with the y-coordinate value of the center of gravity 402. In addition a part of the moving points in a region of interest 202, 203 in the scene can be used to calculate the center of gravity 400, 401, 402 of specific subparts of objects in a region of interest 202, 203, i.e. taking only the 30% of the points on the right side of the global gravity point of a window in the scene.

Based on the coordinates of the bed edges 201*a*, 201*b*, 201*c*, 201*d*, the algorithm defines the two regions of interest 202 and 203*a* and 203*b* mentioned above. The first region of interest 202 is of rectangular shape, with a lower base 204 stretching horizontally across a middle section of the bed 200. The horizontal lower base 204 does not exceed in length the width of the bed 200. In vertical direction the first region of interest 202 stretches beyond a top bed edge 201*a*, with the top bed edge 201*a* being placed at the middle of the first region of interest 202 in vertical direction.

The second region of interest 203*a* and 203*b* is also essentially rectangular in shape, with a lower base 205 stretching horizontally and essentially parallel to the lower base 204 of the first region of interest 202 across the middle section of the bed 200. The horizontal base 205 exceeds the width of the bed 200 by approximately half of the width of the bed 200. In vertical direction the region stretches beyond the top bed edge 201*a*, with the top bed edge 201*a* being placed at the middle of the first region of interest 202 in vertical direction. The total size of the second region of interest 203*a* and 203*b* might be of approximately the same size as the first region of interest 202. However, any suitable size for the regions of interest 202 and 203 can be chosen.

In the following the method is described by which the video component detects automatically the parameters assigned to the different movement types, based on the regions of interest 202, 203 and the centers of motion gravity 400, 401, 402. The result of each parameter detection step is the value of an indicator a calculated according to the design of each parameter. The α value is translated into an individual visual output indicator UI_RGB 300 for each of the detectable parameters (restless, bed exit, torso up etc.) in the range of green to red, which is an [R, G, B] tuple according to the following formula:

UI_RGB=[α*255,(1−α)*255,0].

The output indicator value is used for display in a user interface of the video component. The user interface is not explicitly shown in FIG. 1, but can be any suitable display unit like a screen or the like. In that sense, if the UI_RGB indicator 300 of a specific parameter is closer to red, the parameter is detected to be more prominently present in the frame covered by the camera, e.g. the patient 2 is detected to be closer to the bed edge 201a, 201b, 201c or 201d or the patient 2 is very restless. Conversely, if the UI_RGB indicator 300 of a specific parameter is closer to green, the parameter is detected to be less prominently present in the frame covered by the camera, e.g. the patient 2 is detected to be further away from the bed edge 201a, 201b, 201c 201d or the patient 2 is lying quite still in bed.

In FIGS. 3 to 10, the frame covered by the camera is shown under different conditions of the patient 2. In the display the respective UI_RGB indicators 300 are exemplary arranged in two columns on the left and right sides of the display, with the left side containing an indicator 301 for a "bed exit" event, an indicator 302 for a movement of the patient towards the "bed edge" 201a, 201b, 201c, 201d, an indicator 303 for the upright "torso up" posture and an indicator 304 for "restlessness". On the right hand side an indicator 305 for the video data "risk score" 110 and an indicator 306 for a "fall incident" are arranged. Of course, any other suitable number and arrangement of the UI_RGB indicators 300 is possible. Further, to represent the colors of the UI_RGB indicators 300 clearly in black and white in the figures, an empty square for any of the indicators 300 represents green, while a rising number of dots in the square represents a shift towards red via yellow and orange. A filled square for each of the indicators 300 represents a red color.

Figure 3:
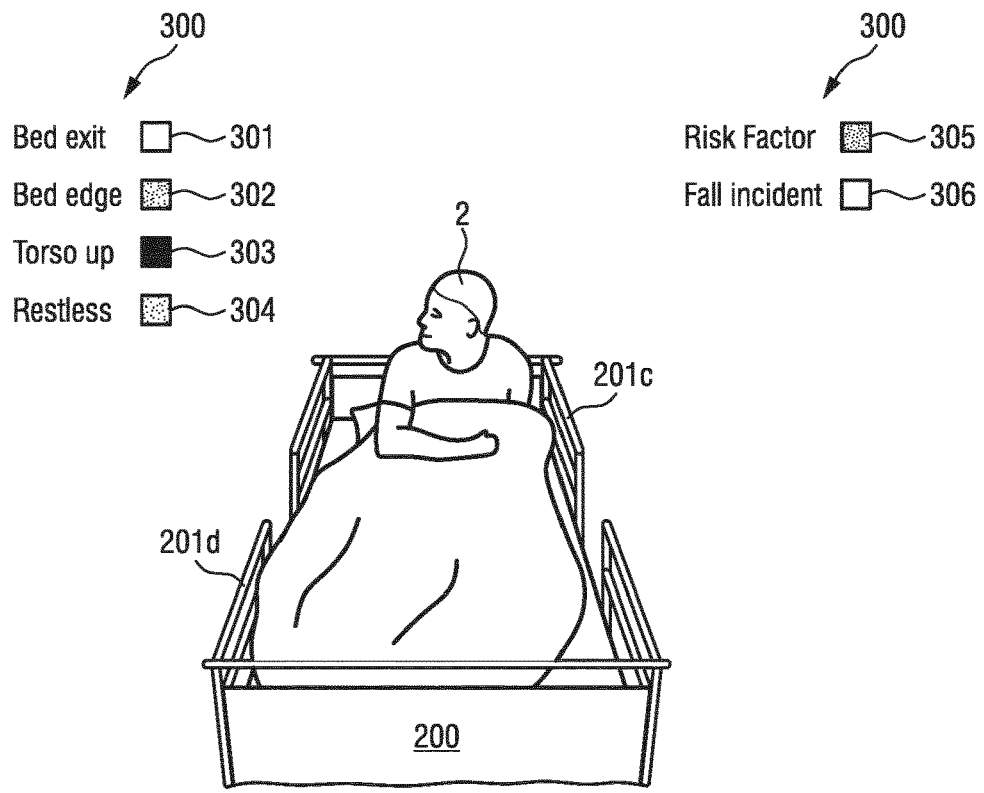
FIGS. 3 to 10 show a patient in bed under different conditions.

Based on the aforementioned regions of interest 202, 203, the video component detects that the patient's torso is up from a lying position when the highest center of motion gravity 402 is located higher than a specific threshold. This specific threshold is below the top boundary of the first region of interest 202 in FIG. 2. This threshold is learned over a set of videos. The situation with the patient's torso being in an upright position is shown in FIG. 3.

The threshold is used to distinguish between a moving point in a scene that appears to be moving due to noise from moving points in the scene that are really representing points of moving objects in the scene. The value of the threshold is calculated by estimating the noise level of the video. That happens based on the average noise level of specific points in the scene when no moving objects are located at those locations in the image. Exemplary, five points at the upper part of a frame are used to calculate the noise of the video, but any set of points scattered over the scene can be used for this calculation. The threshold is calculated in a number of steps.

In case a point which is used to calculate the threshold value is not a point of a moving object in the scene then the variance of the intensity of the point is calculated taking the values of the intensity of the point over the last i.e. 60 frames.

A point which is used to calculate the threshold value of the video is assessed in relation to whether moving objects are located at that point in the scene. That happens by monitoring the intensity change of the point. In case the change of the average value of the intensity of the point, calculated over i.e. the last 60 frames of the video, indicates an abrupt change then the variance of that point over i.e. the last 60 frames of the video is not taken into account in the calculation of the threshold value of the video at that moment of time.

The points that are not rejected based on the considerations described above are used to calculate the variance of the noise level of the video at that moment of time. The variance of the noise level of the video at that moment of time depends on the variance of the points used to calculate the threshold value of the scene. That dependency can be the average of the variances or the maximal value of variances.

The threshold value of the video at that moment of time is then calculated as a multiple of the standard deviation (square root of the aforementioned assessed variance of the video at that moment of time). The multiplication factor is set at 4 (four standard deviations) but it will be based on a training algorithm when field data are available. The training algorithm will be based on training an iterative learning system while using the real videos from the clinical tests.

As can be further recognized in FIG. 3, not only the indicator 303 for the "torso up" posture becomes red when the highest center of motion gravity 402 is higher than the threshold, but also the respective indicator 305 indicating the video data risk score 110 has changed from green to orange, indicating that a fall from the bed 200 might be possible. Likewise, the indicator 302 for approach to the bed edge 201a, 201b, 201c, 201d has changed towards orange since the patient 2 not only sits up but also has shifted slightly to one side of the bed 200. The indicator 304 for restlessness is also slightly away from green, since sitting up will imply a certain amount of movement.

Figure 4:
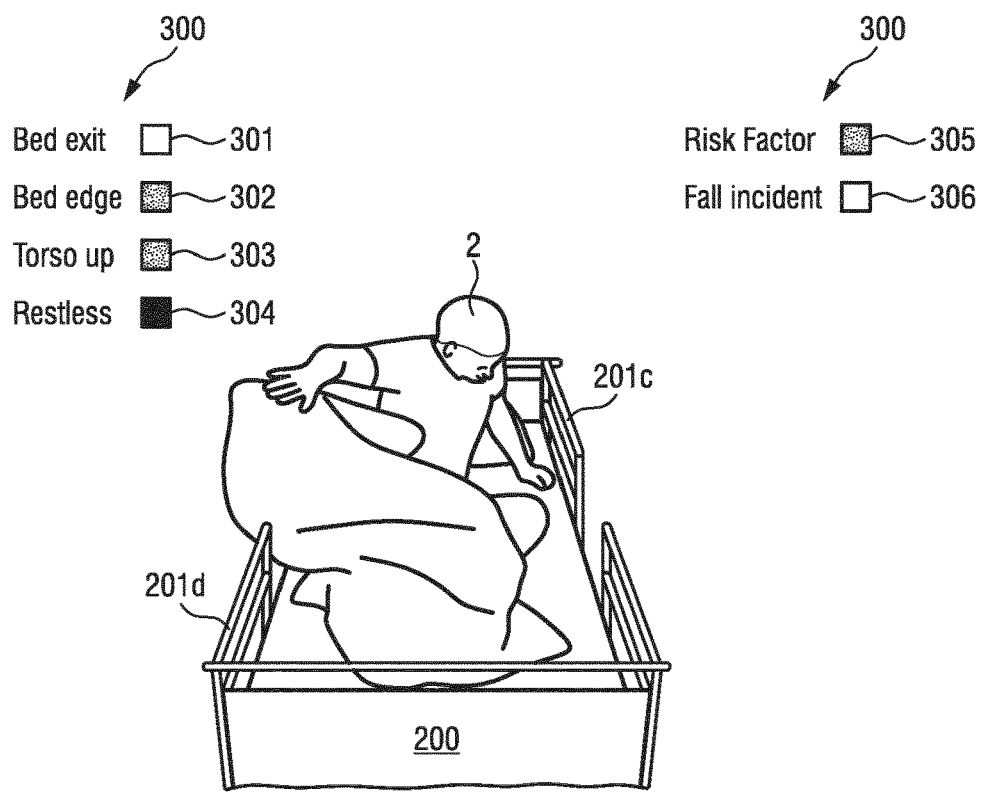

Referring now to FIG. 4, the video component can calculate the variance of the motion of the global center of motion gravity in horizontal direction over a number of consecutive frames, e.g. in a 2 second time interval, to detect restlessness. If this variance is higher than a threshold which can be determined via learning, the video component detects that the patient 2 is restless. The indicator 304 for restlessness in FIG. 4 becomes red when the afore-mentioned variance is higher than the threshold. The further away the variance is from the threshold the further away from red and closer to green the indicator 304 becomes, indicating that the patient 2 is resting quietly. Additionally, the indicators 303 and 302 for "torso up" posture and for the approach of the patient to the bed edge 201 a, 201b, 201c, 201d are changing from green towards orange or red, as does the indicator 305 for the video data risk score 110.

Figure 5A:
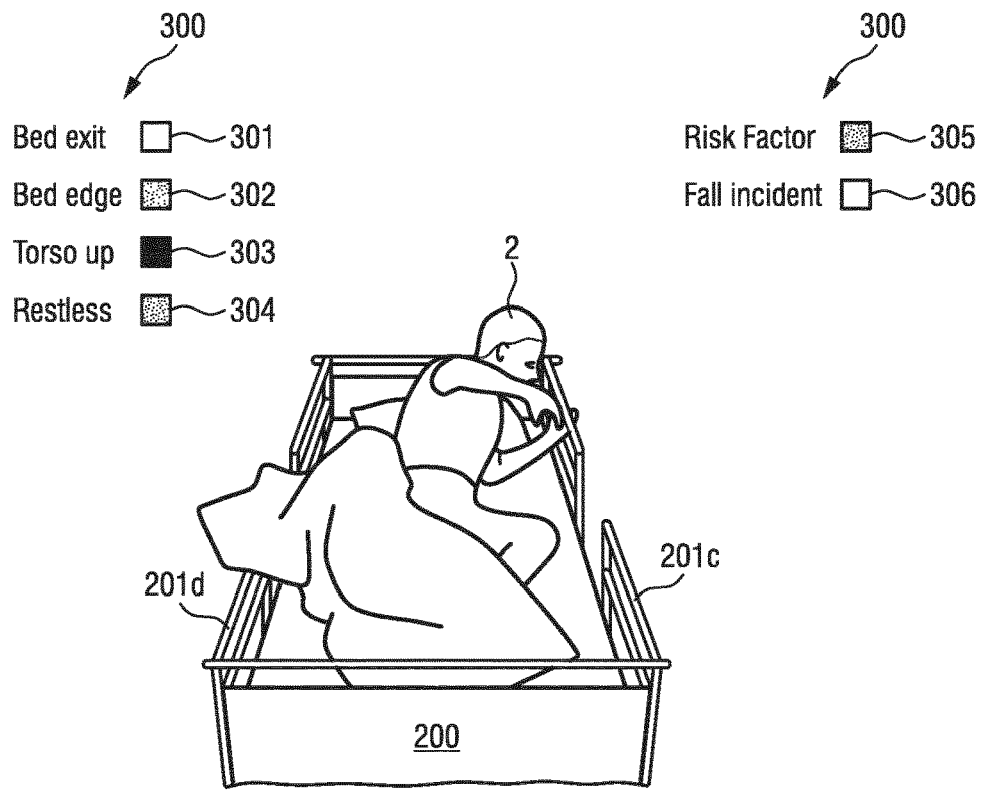
Figure 5B:
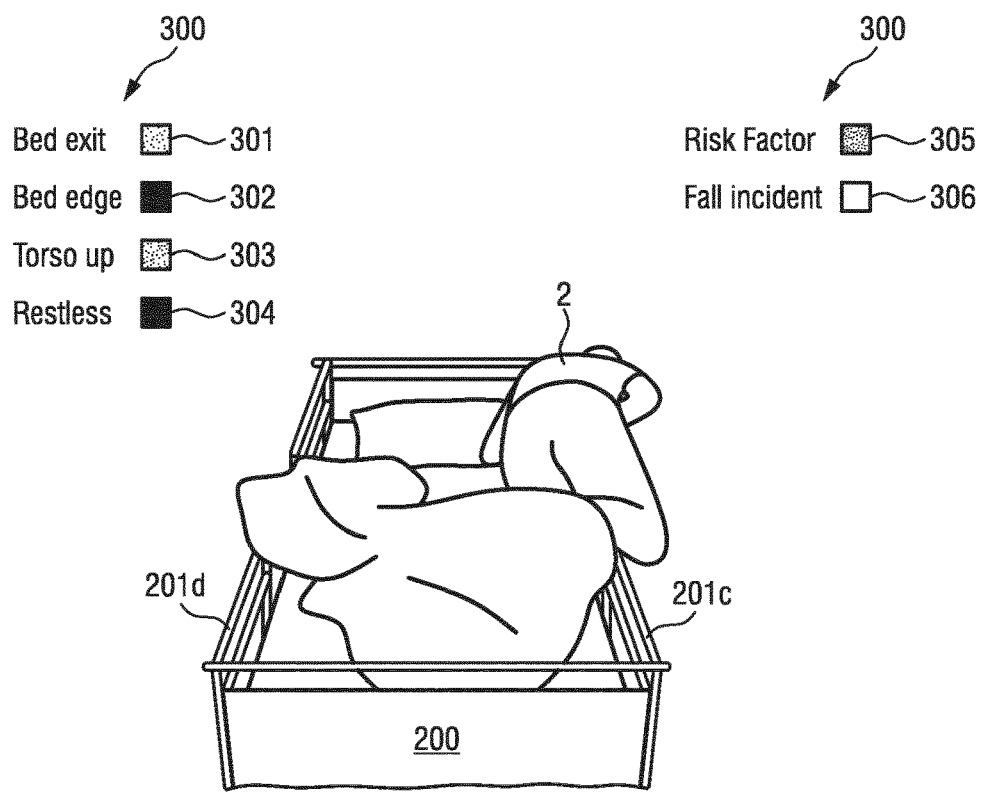

According to FIGS. 5A and 5B, the video component further provides a gradual indicator 302 of the patient's position relative to the vertical bed edges 201c, 201d. In that sense monitoring the patient location relative to the bed edge 201c on the right side is done by monitoring the position of the right most center of motion gravity 401 relative to the right vertical edge of the first region of interest 202 in FIG. 2.

Conversely the video component monitors the patient location relative to the bed edge 201d on the left side by monitoring the position of the left most center of motion gravity 400 relative to the left vertical edge of the first region of interest 202. The values of the indicator 302 are closer to green when the respective center of motion gravity 400, 401 is further away from the vertical edge of the first region of interest 202 on the same side, and is closer to red when the center of motion gravity 400, 401 is closer to that same edge.

Accordingly, FIG. 5A shows the indicator 302 on orange as the patient 2 is touching the bed edge 201c while in FIG. 5B the indicator 302 is red as the patient 2 is climbing on or over the bed edge 201c. Due to the mixture of different movements involved, again other indicators 300 are turning their colors. While in FIG. 5A the "bed exit" indicator 301 is still green as the patient 2 is still in bed 200, the respective indicator 301 turns orange in FIG. 5B when the patient 2 is leaving the bed 200. The indicator 305 for the video data risk score 110 is orange, too. The restlessness indicator 304 is likewise away from green as the action of the patient 2 involves a lot of movement.

Figure 7:
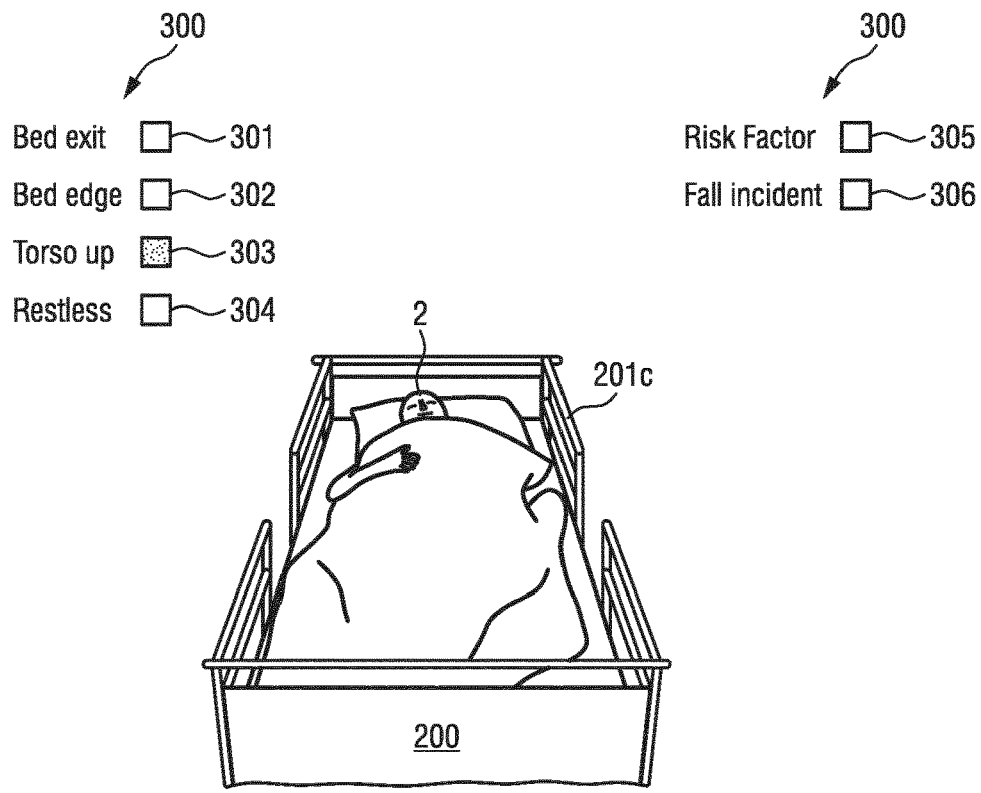

Additionally, the video component can detect that the patient 2 is safe in bed 200 without much movement, e.g. while sleeping or being sedated, when both horizontal centers of motion gravity (right most and left most) 400 and 401 are within the vertical boundaries of the first region of interest 202. This is shown in FIG. 7, where the respective indicators 300 are all green as the patient 2 is not moving.

Figure 6A:
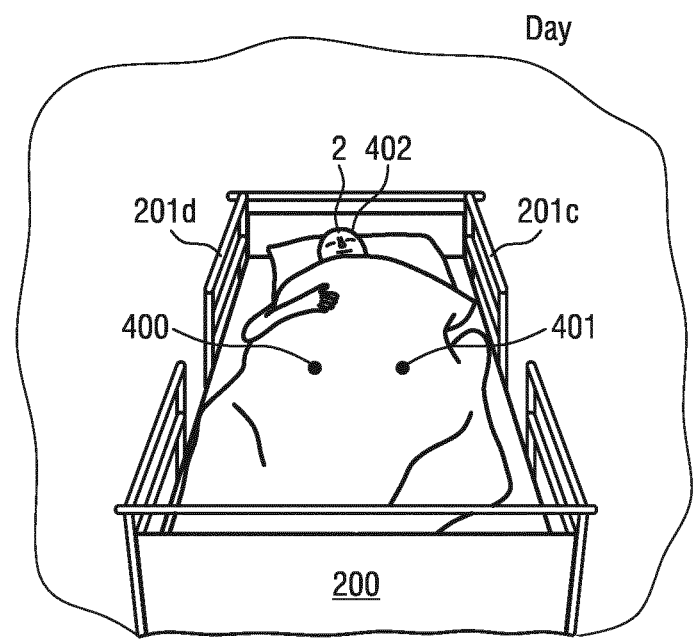
Figure 6B:
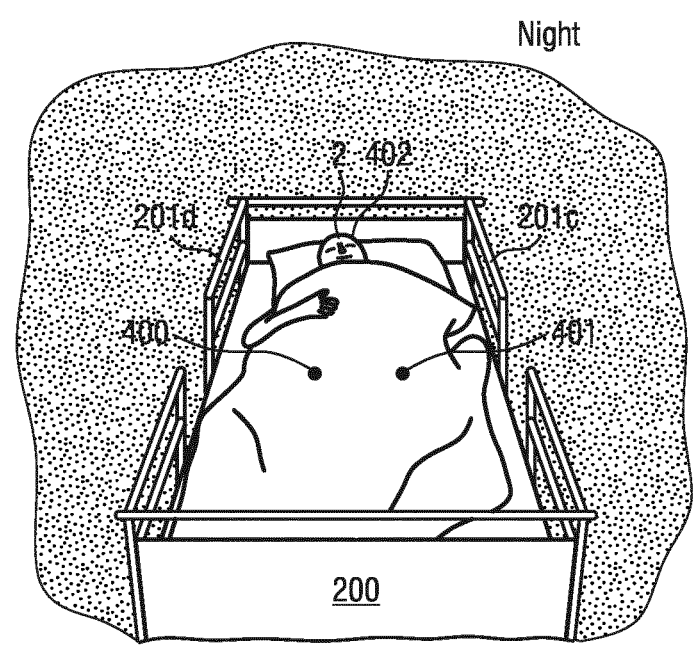

FIGS. 6A and 6B illustrate the video component execution in daylight and night time conditions, where the patient 2 is detected to be safely in bed. No indicators 300 are shown in this case. However, the dots 400 and 401 on the blanket covering the patient 2 represent the two horizontal centers of motion gravity, both found within the confines of the bed edges 201c, 201d, that is, within the vertical boundaries of the first region of interest 202.

Figure 8:
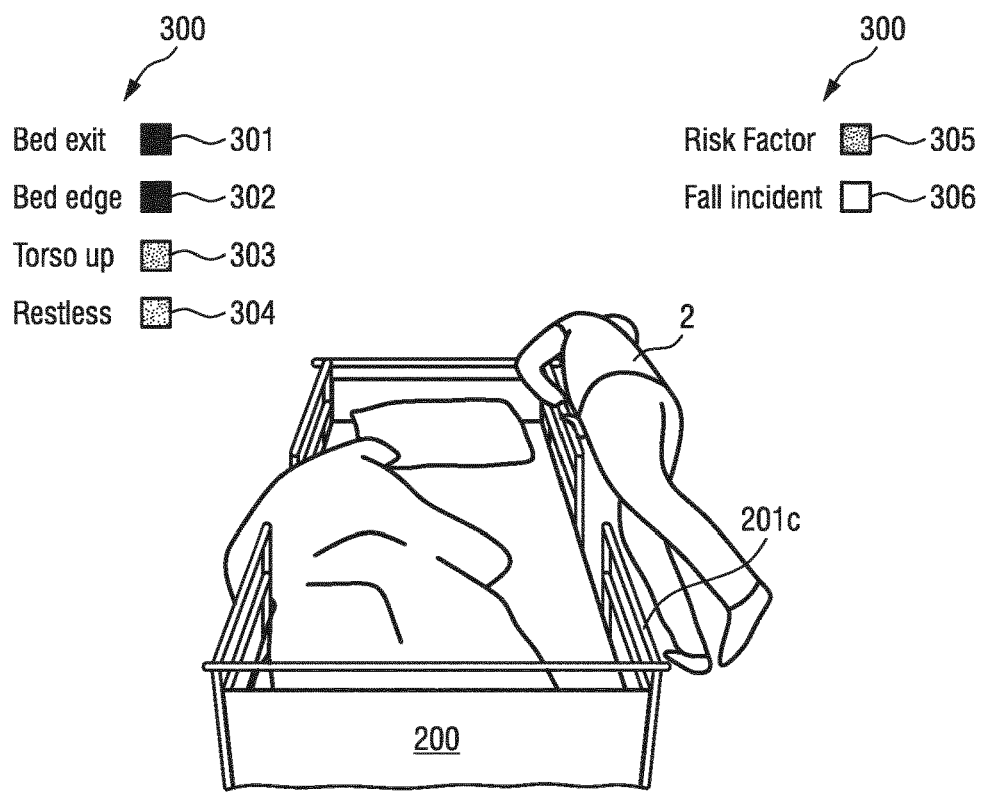
Figure 9:
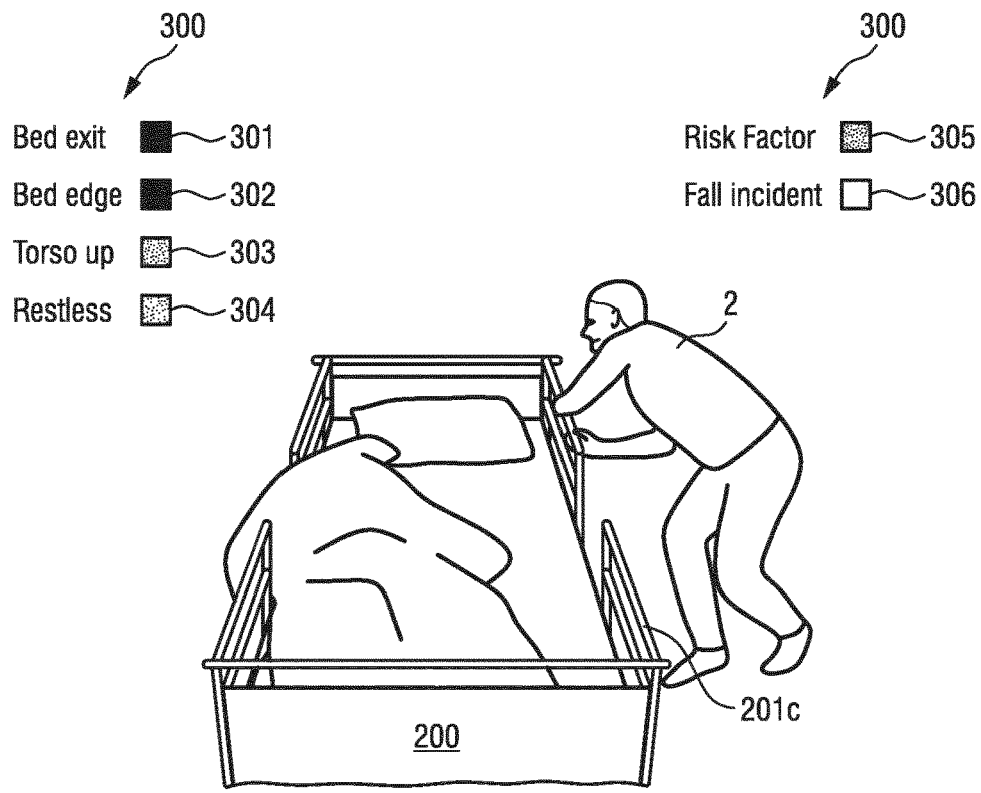

The video component detects that the patient 2 has exited the bed 200 intentionally when the left most center of motion gravity exceeds the right vertical edge of the first region of interest 202 and the right most center of motion gravity 401 exceeds the right vertical edge of the second region of interest 203b. When the aforementioned conditions are met the indicator 301 for "bed exit" becomes red as illustrated in FIGS. 8 and 9. As already detailed above, other indicators 300 may change color in this case, since leaving the bed 200 will involve a lot of movement like bringing up the torso, moving towards the bed edge 201c and thus also triggering the video data risk score 110 to rise.

Figure 10:
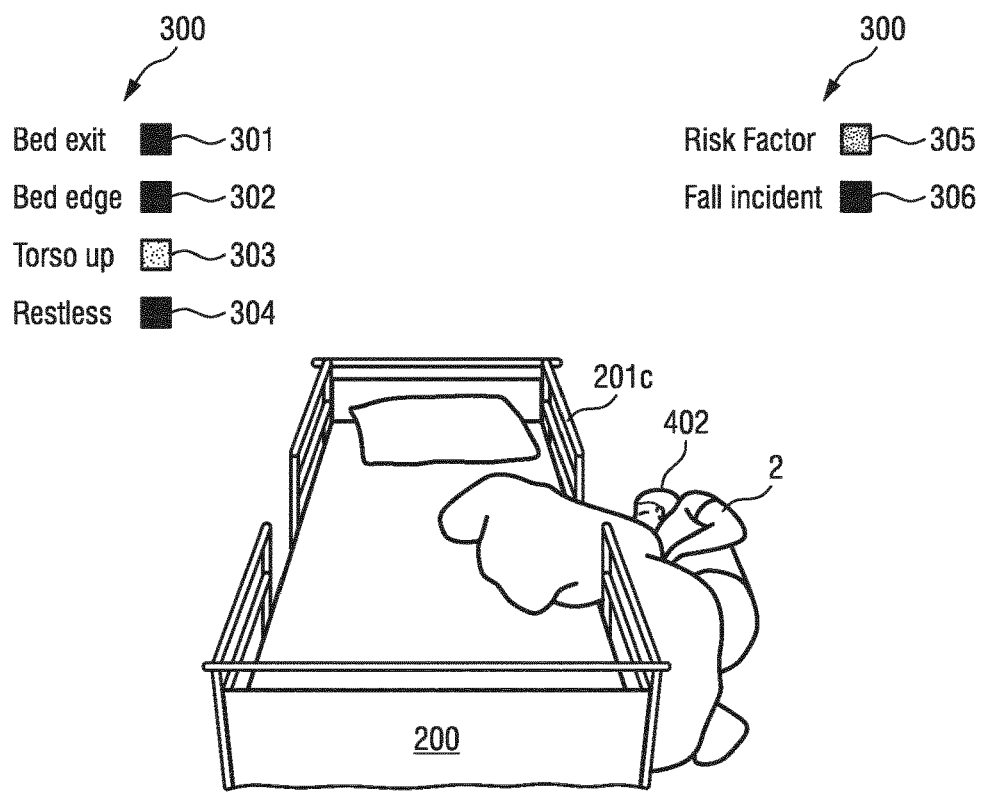

The video component detects that the patient 2 has fallen out of bed 200 when the left most center of motion gravity 400 exceeds the right vertical edge of the first region of interest 202 and the right most center of motion gravity 401 exceeds the right vertical edge of the second region of interest 203b, when the highest center of motion gravity 402 is located below a certain horizontal threshold placed below the bases 204 and 205 of the regions of interest 202 and 203. The threshold is determined via learning over a number of videos. When the aforementioned conditions are met the indicator 306 for "bed fall" becomes red as illustrated in FIG. 10. Other indicators 300 are involved again and change color, only the "torso up" indicator 303 is green since the patient 2 is now lying outside the bed 200, but with torso down.

The calculation of the video data risk score 110 indicating the allover bed fall risk is based on a linear combination or sum of all the detected parameters except fall detection, divided by the number of risk factors detected (No_RF) taken into calculation. In the examples shown in the FIGS. 3 to 10, the number of risk factors is three (No_RF=3):

Video data risk score=(Torso Up+Restless+Bed Edge)/No_RF

In the following, the functionality of the vital signs sensor 13 is described in detail. In the following, analogous to the video component, the vital signs sensor 13 and the respective vital signs processing unit 9 are termed "vital signs component". The processing unit 9 receives input from the vital signs sensor 13 in the patient room 40 as described with reference to FIG. 1 above.

This part of the device 1 receives input from the vital signs sensor 13 which is arranged in the patient room 40 or directly on the body of the patient like e.g. a pulsemeter, a device for monitoring blood pressure or the like. Alternatively, the vital signs sensor 13 can be a remote sensor, e.g. a PPG sensor, which can monitor the blood oxygen content by way of irradiating certain skin areas. The vital signs component again like the video component combines two functions. On the one hand, the reliability of the vital signs or physiological signals (e.g. heart signal, respiration signal, accelerometer signals etc.) is assessed, on the other hand, the system detects in real time the presence of risk factors based on which it calculates a risk score indicating the likelihood of a bed fall incident. This functionality is executed only if the reliability of the physiological signals as mentioned above is determined to be sufficient.

The modifiable risk factors detected in real-time are the following: the patient experiences tension or stress, the patient experiences anxiety, the patient experiences restlessness, i.e. is tossing and turning, or the patient experiences agitation, which might be expressed via intense or fast, large, erratic movements. Further, the patient's posture in bed space can be detected: patient's torso is up, the patient is leaning over the bed edge or the patient is reaching out of bed.

Detecting the modifiable risk factors above allows calculating a vital signs risk score 111 for a bed fall incident based on the input from the vital signs sensor 13. The Vital signs risk score 111 in the following is denoted with R_VitalSigns. If the vital signs sensor is not reliable the system 11 does not process the signal at all and R_VitalSigns is set on −1 to indicate that the risk has not been assessed due to signal unreliability.

The assessment of the reliability of the physiological signals received from the vital signs sensor is done by way of a variable to express the vital signs sensor reliability SR_VS. SR_VS is set on 1 when the sensor reliability is assessed to be sufficient and 0 otherwise.

The assessment is based on the signal broadcasting rate as well as on the rate of signal artefacts. In that sense whenever the signal broadcasting rate is below a threshold defined as system requirements (e.g. 1 Hz), the signal of the vital signs sensor 13 is determined to be not reliable and SR_VS is set to 0. Similarly, if the rate of signal artefacts is above a threshold, e.g. the proportion of outlier samples within a moving time window is higher than a threshold, that is, for instance, more than 10% of samples are outliers within a 1 minute window, the signal of the vital signs sensor 13 is determined to be not reliable and SR_VS is set to 0.

If however the signal broadcasting rate as well as the signal artefacts rate is within acceptable ranges relative to the thresholds mentioned above, SR_VS is set to 1.

This physiological signals reliability assessment could be done either punctually with a certain frequency or at certain intervals or continuously using a moving signal window. The latter option implies buffering small portions of the signals to be assessed and helps to streamline processor performance.

In the following, the detection of risk factors and calculation of the risk score based on the vital signs data 140 is described.

The vital signs component executes on the dedicated processing unit 9 and receives input from the vital signs sensor 13 based on which it detects in real-time a number of risk factors known to lead to bed-fall incidents as mentioned above. The component uses the detection of the risk factors above to calculate a vital signs risk score R_VitalSigns 111 indicating in real time the chance for a bed fall incident. The output of the respective component thus includes the SR_VS signal reliability indicator and the R_VitalSigns risk score 111.

If the patient 2 experiences some tension or stress, the respective risk factor is detected by analyzing the heart rate (HR), heart rate variability (HRV), respiration rate (RSP Rate) and accelerometer (ACC) signals in the following manner: the system detects within a time window longer than a threshold (e.g. 0.5 mins) an increasing trend of slightly elevated average values relative to the baseline average (e.g. less than 5% increase) for HR, RSP Rate, and slightly lower values for HRV, but the system 11 does not detect significant movement in the ACC signal. The accelerometer preferably is arranged on the patient's 2 chest, but can also be arranged on other suitable locations of the body.

If the patient 2 experiences anxiety, the system detects within a time window longer than a threshold (e.g. 0.5 mins) an increasing trend of significantly elevated average values relative to the baseline average (e.g. larger than 5% increase) for HR, RSP Rate, and lower values for HRV, but the system does not detect significant movement in the ACC signal.

Further, the patient's posture in bed 200 is used to determine a respective risk factor as describe with reference to FIGS. 11 to 15.

Figure 11:
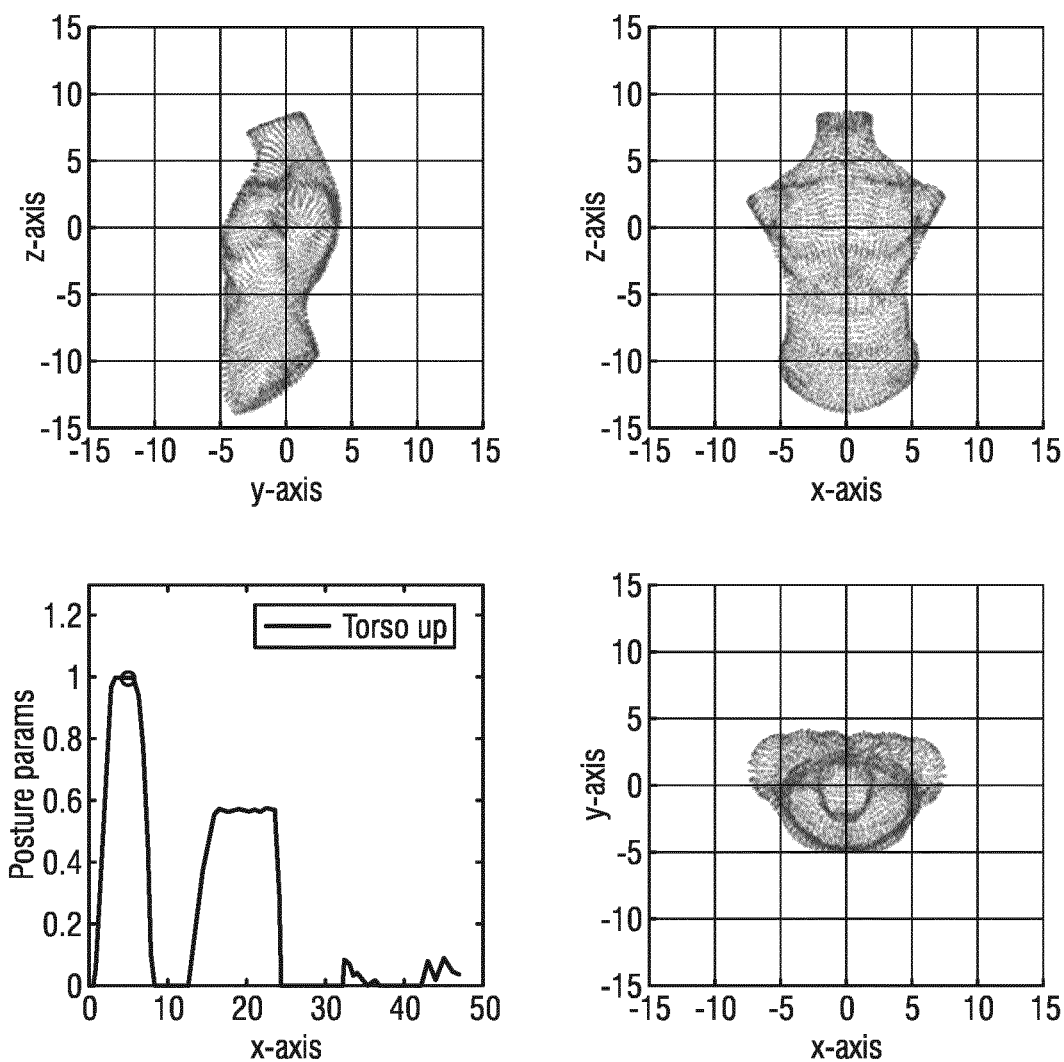
FIGS. 11 to 13 show diagrams of accelerometer signals of certain patient's postures and movements.

In case the patient 2 sits up in the bed 200, the "Torso up" signal from FIG. 11 is calculated by applying the following formula (1) to the x, y, z accelerometer signals:

$$\text{Torso up} = \sin(\varphi) = \frac{-tn_y}{\sqrt{tn_x^2 + tn_y^2 + tn_z^2}} \quad (1)$$

with $$tn_i = \frac{lcounts_i - cming_i}{cplusg_i - cming_i} \cdot 2 - 1$$

Therein, $lcounts_i$ (i representing the x, y, z, channel number) are low-pass filtered accelerometer counts, cut-off=1 Hz, $cming_i$ =lcounts for −g acceleration, $cplusg_i$=lcounts for +g acceleration.

The preceding formula is used for normalization of the accelerometer counts "lcounts" to yield normalized values "tn" ranging from "−1" (if the gravity acceleration is pointing into the negative coordinate direction) to "+1" (if the gravity acceleration is pointing into the positive coordinate direction). The "+x" direction points from the patient's chest towards his left side, the "−x" direction towards his right side. The "+y" direction points towards his head, the "−y" direction towards his feet. The "+z" direction points outward from the chest, the "−z" direction points from his chest towards his back. Example: A normalized accelerometer reading of (0; 0; −1) of a patient in rest would indicate a "supine" position, whereas a reading of (0; −1; 0) would indicate a "torso up" position.

The system 11 detects that the patient 2 has his torso up when the Torso Up signal reaches a peak value larger than 0.7 as illustrated in FIG. 11. The round marker in the bottom left part of FIG. 11 indicates the current "torso up" situation illustrated along the three axes in the remaining three parts of FIG. 11.

Figure 12:
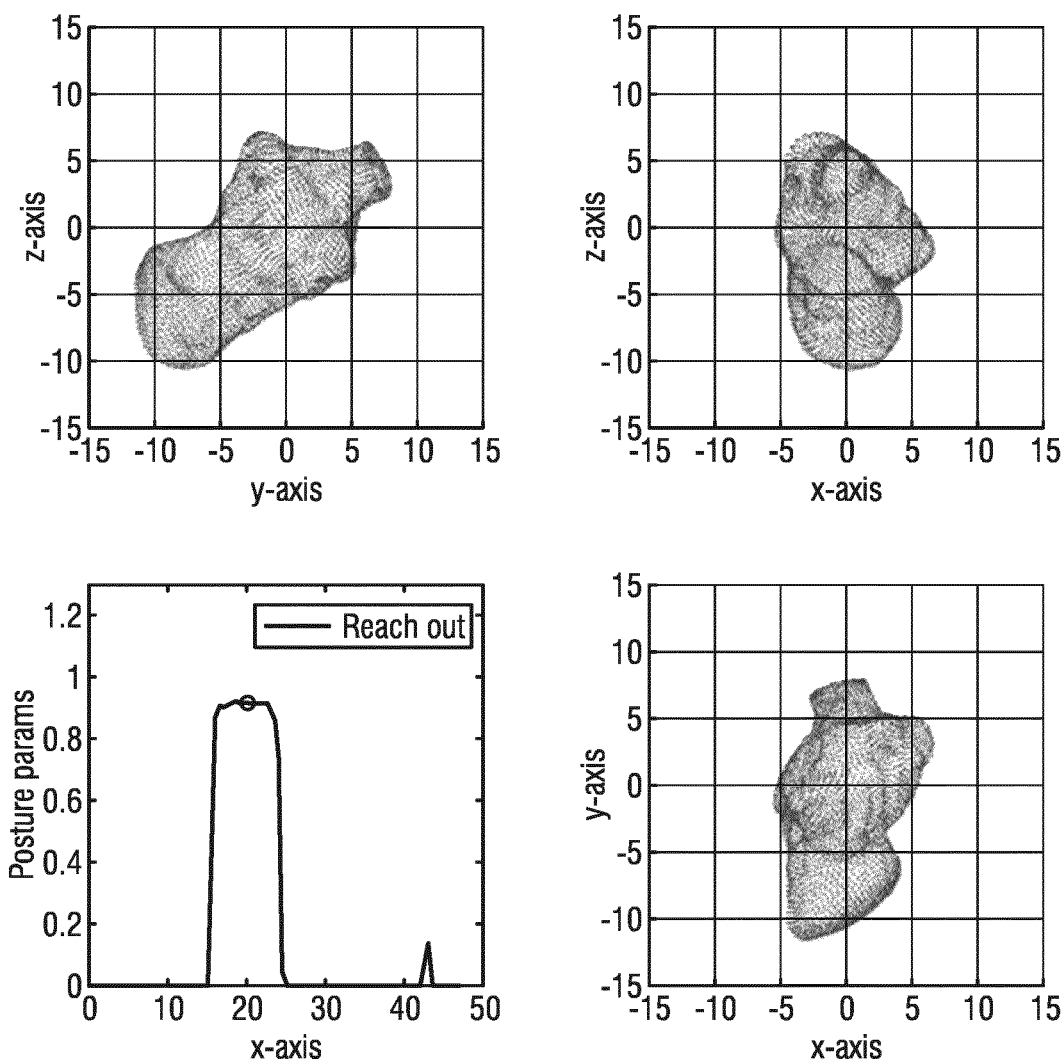

If the patient reaches out of the bed, the "Reach out" signal from FIG. 12 is calculated by applying formula (2) to the x, y, z accelerometer signals:

$$\text{Reach out} = |\sin(2\psi)| \cdot (tn_z > 0) \cdot \sin(2\varphi) \cdot (tn_y < 0) \quad (2)$$

with $$\sin(2\psi) = \frac{2 \cdot |tn_x \cdot tn_z|}{tn_x^2 + tn_z^2}$$

and $$\sin(2\varphi) = \frac{-2 \cdot tn_y \cdot \sqrt{tn_x^2 + tn_z^2}}{tn_x^2 + tn_y^2 + tn_z^2}$$

The first factor in "Reach out" (=|sin(2ψ)|*($t_z$>0)) is thus at maximum (=1) if ψ=45 deg and $t_z$>0. The second factor in "Reach out" (=sin(2φ)*($t_y$<0)) is at maximum (=1) if φ=45 deg and $t_y$<0.

The system 11 detects that the patient 2 is reaching out when the Reach Out signal reaches a peak value larger than 0.8 as illustrated in FIG. 12. The round marker in the bottom left part of FIG. 12 indicates the current "reach out" situation illustrated along the three axes in the remaining three parts of FIG. 12.

Figure 13:
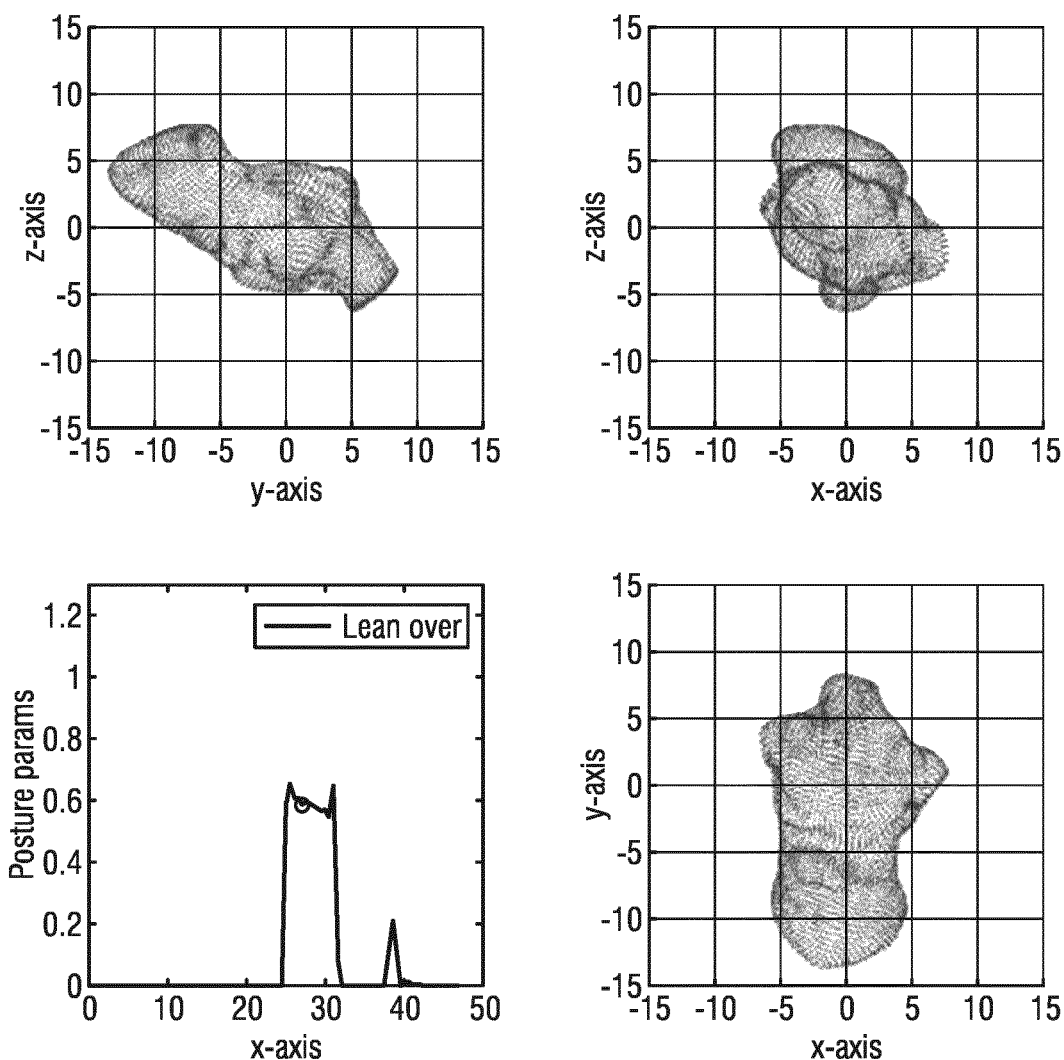

If the patient 2 is leaning over the bed edge 201, the "Lean over" signal from FIG. 13 is calculated by applying formula (3) to the x, y, z accelerometer signals:

$$\text{Lean over} = |\sin(2\psi)| \cdot (tn_z > 0) \cdot -\sin(2\varphi) \cdot (tn_y > 0) \quad (3)$$

with $$\sin(2\psi) = \frac{2 \cdot |tn_x \cdot tn_z|}{tn_x^2 + tn_z^2}$$

and $$\sin(2\varphi) = \frac{-2 \cdot tn_y \cdot \sqrt{tn_x^2 + tn_z^2}}{tn_x^2 + tn_y^2 + tn_z^2}$$

The first factor in "Lean over" (=|sin(2ψ)|*($t_z$>0)) is thus at maximum (=1) if ψ=45 deg and $t_z$>0. The second factor in "Lean over" (=−sin(2φ)*($t_y$>0)) is at maximum (=1) if φ=−45 deg and $t_y$>0.

The system 11 detects that the patient 2 is leaning over when the Lean Over signal reaches a peak value larger than 0.5 as illustrated in FIG. 13. The round marker in the bottom left part of FIG. 13 indicates the current "lean over" situation illustrated along the three axes in the remaining three parts of FIG. 13.

Figure 14:
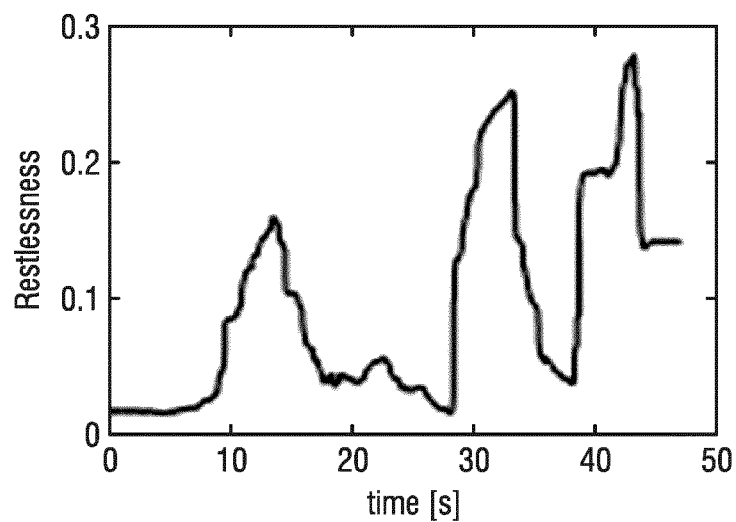
FIG. 14 shows a restlessness diagram of a patient.

Restlessness is defined as a motion where the patient torso is orientated horizontally, and movement amplitude is limited and predominant on the x and z axes referring to tossing and turning movements of the body. If the patient 2 experiences restlessness, the "restlessness" signal illustrated in FIG. 14 is obtained by applying formula (4) to the x, y, z accelerometer signals.

$$\text{Restlessness} = \text{Movav}(50 \cdot Rm, 5\text{ s}) \quad (4)$$

with $rm = \sqrt{rn_x^2 + rn_y^2 + rn_z^2} \cdot (1 - \text{TorsoUp})$,
where Torso Up is defined in formula (1) above and $$rn_i = \frac{hcounts_i}{cplusg_i - cming_i} \cdot 2$$

where movav(A,T) is a moving average of A over time T, hcounts$_i$ represents a high-pass filtered accelerometer counts (i is x, y, or z accelerometer channels), with cutoff=2 Hz.

The quantity "rni" are normalized, high-pass filtered accelerometer signals for each coordinate direction i. Then the magnitude of the vector given by the individual components rni is calculated, i.e. a quantity indicating rapidly varying accelerations of the patient 2. But the patient 2 could also perform "normal" activities like walking, running or jumping. All these "normal" activities would be characterized by a "TorsoUp" signal close to 1, whereas "restlessness" of a patient lying in bed would be characterized by a "TorsoUp" signal close to 0. Therefore, the definition of "rm" includes a factor "(1−TorsoUp)" to suppress the mentioned "normal" activities in the calculation of "restlessness". During phases of restlessness the signal "rm" is rapidly oscillating between 0 and its maximum value, therefore finally a "moving average" operation "movav" is performed, i.e. averaging the signal "rm" (multiplied by an arbitrary factor 50) over the last 5 s to obtain the "Restlessness" signal.

In FIG. 14, restlessness is expressed via a signal obtained by means of applying formula (1) to the x, y, z accelerometer signals.

Patient agitation is defined as a motion where the patient torso is orientated vertically, and movement amplitude is high, especially significantly higher than in the case of restlessness as in FIG. 14, and predominant on the y and x axes. Agitation is expressed via intense/fast, large, erratic movements.

This is modeled by the following formula (5)

$$\text{Agitation} = \text{movav}(50 \cdot rm, 5\text{ s}) \quad (5)$$

with $rm = \sqrt{rn_x^2 + rn_y^2 + rn_z^2} \cdot \text{TorsoUp}$, where Torso Up is defined in formula (1) above
and $$rn_i = \frac{hcounts_i}{cplusg_i - cming_i} \cdot 2$$

where movav(A,T) is a moving average of A over time T, hcounts$_i$ represents a high-pass filtered accelerometer counts (i is x, y, or z accelerometer channels), with cutoff=2 Hz.

Figure 15:
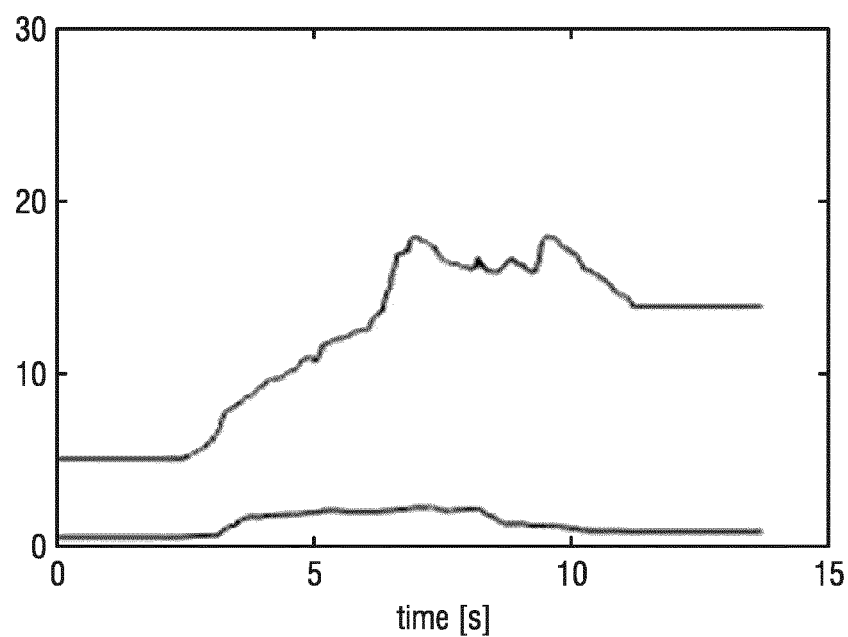
FIG. 15 shows a diagram comparing restlessness and agitation of a patient.

In FIG. 15, a combined illustration of restlessness and agitation signals shows the amplitude of movement at agitation being significantly higher than in the case of restlessness (upper graph in FIG. 15).

Calculation of the R_VitalSigns risk score 111 is based on assessing the risk factors above, where the R_VitalSigns is increased by a parameter xi (i=1 . . . 8)—associated with each risk factor. This would imply the following tests and associated computations:

If Stress detected=yes then

Risk Score=Risk Score⊗x1

If Anxiety detected=yes then

Risk Score=Risk Score⊗x2

If Patient TorsoUp detected=yes then

Risk Score=Risk Score⊗x3

If Patient ReachOut detected=yes then

Risk Score=Risk Score⊗x4

If Patient Lean Over detected=yes then

Risk Score=Risk Score⊗x5

If Patient Restlessness detected=yes then

Risk Score=Risk Score⊗x6

If Patient Agitation detected=yes then

Risk Score=Risk Score⊗x7 wherein in a simple example "⊗" could stand for a simple sum.

There are, however, other possibilities to connect the risk scores. The actual formula will be learned from the data, i.e. from the different occurrence of the single parameters.

At system initialization parameters x1 to x7 can be initialized based on values indicated by literature studies, while over time, the system 11 adjusts the parameters values by learning the influence of each risk factor above on a bed fall occurrence, for the specific population at hand. This is done by executing correlation analyses and applying regression techniques after each bed fall incident to understand the impact of each risk factor on the likelihood of a bed fall event and to update the values of the parameters above. As time passes the system 11 will thus become increasingly accurate in determining the risk score. If no bed fall incident occurs no parameter adjustment is needed.

In the following, the intervention unit 15 will be described in more detail. The intervention unit 15 preferably is located in the workstation room 50 away from the patient rooms 40 to allow access for the medical staff and the maintenance staff alike and to allow monitoring of many individuals simultaneously. The intervention unit 15 receives as input the patient profile from the classification unit 10 and the total risk score 114 as described above calculation unit 6.

Based on those values (e.g. total risk score 114 is above a threshold or increasing significantly within a short time window) the intervention unit 15 performs one or more of the following actions:

Either it contacts the patient via the feedback unit 14 in the patient room 40 and assesses the situation, attempts to calm the patient 2 if necessary, persuades the patient 2 to remain in bed 200, while medical staff is on the way to attend to the patient's needs.

Alternatively or simultaneously, the intervention unit identifies the nearest available medical staff and sends the above information to that staff member to ensure speed of action. In order to identify the staff nearest to the patient room 40 the intervention unit 15 may use locating technologies (e.g. GPS). In order to identify the staff available at the time, the intervention unit 15 consults a staff schedule 17 which might be stored in a database indicating the staff availability at that time.

The intervention unit 15 in any case ends the medical staff an alarm code indicating risk for bed fall incident with intervention needed.

Intervention information indicating details regarding the patient profile and the recommended intervention for this particular patient given profile may also be sent by the intervention unit 15.

Besides, the intervention unit 15 informs medical staff regarding the timeframe within an intervention needs to be provided in order to be effective and prevent the incident.

Further, the intervention unit 15 helps prioritize the current patient needs above other prospective activities.

The intervention unit 15 is part of the larger infrastructure responsible for patient monitoring, bed fall risk assessment, patient classification based on profile and adaptive intervention as described in FIG. 1.

The intervention unit 15 makes use of an artificially intelligent implementation that employs e.g. speech recognition for direct communication with the patient 2 when needed. The system distinguishes 3 situations relevant in this context:

1. The total risk score 114 is low or moderate (below a certain threshold) but slow to moderately increasing within a limited time-window—e.g. risk score values rise under an average slope of a maximum 10 degree angle (average slope<=0.17) during the last 10 minutes.

2. The total risk score 114 is low or moderate (below a certain threshold) but significantly increasing within a limited time-window (e.g. 5-10 minutes)—e.g. risk score values rise under an average slope of an angle larger than 10 degrees (average slope>0.17).

3. The total risk score 114 is determined to be high (above a certain threshold).

The intervention unit 15 reacts in each situation described above based on information derived from the patient profile. In that sense, the system classifies the patient 2 in terms of Cognitive Ability Level (CgAL), Communication Ability Level (CmAL) and Compliance Level (CL). If based on the patient profile, patient does not have a cognitive impairment and no speech impairment CgAL is set to High. In any other situation it is set to Low. In addition, based on the patient profile (specifically the psychological compliance profile) the system sets CL to High or Low.

In the following tables, the situations by which the intervention unit 15 reacts to the value trends of the total risk score 114 are described.

1. If the total risk score 114 is low or moderate (below a certain threshold) but slow to moderately increasing within a limited time-window (e.g. 10 minutes), the intervention unit 15 makes a projection based on current risk score growth how long until the total risk score 114 will become high to indicate to the nurse the time frame available for an effective prevention. This will help with prioritizing the patients that need attendance.

TABLE 1

| No | CgAL | CmAL | CL | eSitter intervention |
|---|---|---|---|---|
| 1. | High | High | High | Intervention unit 15 communicates with patient 2 e.g. via audio: enquires patient if he/she has needs that must be attended to, records patient response (AV stream), gently suggests patient 2 to wait safely in bed, and that a nurse on duty is informed right away. Intervention unit 15 contacts the nurse on duty and sends to their mobile phone a message specifying that bed fall risk grows, plays the record of the patient indicating their needs, indicates to nurse the time frame she should attend to patient need in order to prevent an incident. Intervention unit 15 keeps in touch reassuring patient 2 by updating on how long it takes until nurse attends to needs. |
| 2. | High | High | Low | Intervention unit 15 communicates with patient 2 e.g. via audio: enquires patient if he/she has needs that must be attended to, records patient response (AV stream), advises patient 2 to wait safely in bed, and that a nurse on duty is informed right away. Intervention unit 15 contacts the nurse on duty and sends to their mobile phone a message specifying: bed fall risk grows, patient 2 is non-compliant, plays the record of the patient 2 indicating their needs, indicates to nurse the time frame she should attend to patient need in order to prevent an incident. Intervention unit 15 keeps in touch with patient 2 by updating on how long it takes until nurse attends to needs. |
| 3. | High | Low | High | Intervention unit 15 communicates with patient 2 e.g. via audio and gently suggests patient 2 to wait safely in bed, and that a nurse on duty is informed right away. Intervention unit 15 contacts the nurse on duty and sends to their mobile phone a message specifying: bed fall risk grows, patient 2 is not able to verbally communicate, indicates to nurse the time frame she should attend to patient need in order to prevent an incident. Intervention unit 15 keeps in touch reassuring patient 2 by updating on how long it takes until nurse attends to needs. |
| 4. | High | Low | Low | Intervention unit 15 communicates with patient 2 e.g. via audio and gently suggests patient 2 to wait safely in bed, and that a nurse on duty is informed right away. Intervention unit 15 contacts the nurse on duty and sends to their mobile phone a message specifying: bed fall risk grows, patient 2 is not able to verbally communicate, patient 2 is non-compliant, indicates to nurse the time frame she should attend to patient need in order to prevent an incident. Intervention unit 15 keeps in touch reassuring patient 2 by updating on how long it takes until nurse attends to needs. |

TABLE 1-continued

| No CgAL | CmAL | CL | eSitter intervention |
|---|---|---|---|
| 5. Low | High | High | Intervention unit 15 communicates with patient 2 e.g. via audio, addressed patient 2 gently indicating medical staff will attend very soon (AV stream). Additional calming stimuli could be provided (e.g. gentle nature sounds or music), while intervention unit 15 maintains touch with patient and keeps reassuring.<br>Intervention unit 15 contacts the nurse on duty and sends to their mobile phone a message specifying: bed fall risk grows, patient 2 is cognitively impaired, patient 2 can be communicated with, indicates to nurse the time frame she should attend to patient need in order to prevent an incident, indicates to nurse she needs to give this patient 2 even higher priority given higher unpredictability induced by cognitive impairment, recommends staff on ways of approaching the patient given cognitive impairment, that likely patient 2 might start feeling disoriented, confused and/or anxious. |
| 6. Low | High | Low | Similar to No. 5. except that medical staff is informed patient 2 is not compliant. |
| 7. Low | Low | High | Similar to No. 5. except that medical staff is informed patient 2 cannot communicate. |
| 8. Low | Low | Low | Similar to No. 5. except that medical staff is informed patient 2 cannot communicate and is not compliant. |

2. If the total risk score 114 is low or moderate (below a certain threshold) but significantly increasing within a limited time-window (e.g. 5-10 minutes), the intervention unit 15 again makes a projection based on current risk score growth how long until the total risk score 114 will become high to indicate to the nurse on duty or nearest available medical staff the time frame available for an effective preventive intervention. This will help with prioritizing the patients 2 that need attendance.

The intervention matrix is similar to the one specified in Table 1 with the difference that in this case the patient automatically becomes highest priority for nurses on duty, and if all nurses on duty engaged with other patients 2 and unable to attend the nearest available medical staff is contacted.

3. If the total risk score 114 is determined to be high (above a certain threshold), differences with regard to the previously described situations occur. Action is immediately required. The intervention unit 15 simply identifies the nearest available medical staff and informs nurses on duty as well that patient needs to be attended.

TABLE 2

| No CgAL | CmAL | CL | eSitter intervention |
|---|---|---|---|
| 1. High | High | High | Intervention unit 15 communicates with patient 2 e.g. via audio: enquires reason for impending bed exit and records patient response (AV stream), gently suggests patient 2 to wait safely in bed, and that medical staff will attend his/her need soon.<br>Intervention unit 15 locates nearest available medical staff and sends to their mobile phone a message with high importance specifying: alarm code for bed fall, plays the record of the patient 2 indicating their needs; depending on the need expressed by patient, intervention unit 15 recommends a course of action for the staff to consider.<br>Intervention unit 15 keeps in touch reassuring patient 2 by updating on how long it takes until medical staff arrives. Alternatively the video UI interface could display the hospital map and as a progressing dot the position of the approaching staff to the patient room 40. |
| 2. High | High | Low | Intervention unit 15 communicates with patient 2 e.g. via audio, emphasizes to patient 2 the necessity to remain in bed (AV stream) until attended due to risk fall.<br>Intervention unit 15 locates nearest available medical staff and sends to their mobile phone a message with high importance specifying: alarm code for bed fall, indicates that patient 2 can be communicated with but has low compliance and immediate attendance is required, recommends staff on ways of approaching the patient regarding persuasion techniques.<br>Intervention unit 15 keeps in touch with patient 2, indicating that the medical staff "will be with you any moment, please do not leave your bed". |
| 3. High | Low | High | Intervention unit 15 communicates with patient 2 e.g. via audio: gently suggests patient 2 to wait safely in bed, and that medical staff will attend his/her need soon.<br>Intervention unit 15 locates nearest available medical staff and sends to their mobile phone a message with high importance specifying: alarm code for bed fall. |

TABLE 2-continued

| No | CgAL | CmAL | CL | eSitter intervention |
|---|---|---|---|---|
| | | | | Intervention unit 15 keeps in touch reassuring patient 2 by updating on how long it takes until medical staff arrives. Alternatively the video UI interface could display the hospital map and as a progressing dot the position of the approaching staff to the patient room 40. |
| 4. | High | Low | Low | Similar to No. 2. |
| 5. | Low | High | High | Intervention unit 15 communicates with patient 2 e.g. via audio, addressed patient 2 gently indicating medical staff will attend very soon (AV stream). Additional calming stimuli could be provided (e.g. gentle nature sounds or music), while intervention unit 15 maintains touch with patient 2 and keeps reassuring. Intervention unit 15 locates nearest available medical staff and sends to their mobile phone a message with high importance specifying: alarm code for bed fall, indicates that patient can be communicated with but has low cognitive ability and immediate attendance is required, recommends staff on ways of approaching the patient given cognitive impairment, that likely patient 2 feels disoriented, confused and/or anxious. |
| 6. | Low | High | Low | Similar to No. 5. |
| 7. | Low | Low | High | Similar to No. 5. except that medical staff is informed patient 2 cannot communicate. |
| 8. | Low | Low | Low | Similar to No. 5. except that medical staff is informed patient 2 cannot communicate and is not compliant. |

As mentioned before, the feedback unit 14 (referred to by "communicates by audio" in tables 1 and 2) can be a TV set usually available in hospital rooms nowadays. However, if the environment e.g. is a nursing home for cognitively impaired persons the feedback unit can be a display with speakers, microphone and further means of communication arranged in a suitable location near the patient 2.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device for detection of a bed fall risk of an individual, the device comprising:
    a vital signs sensor configured to obtain vital signs sensor data related to a vital sign of the individual;
    a processing unit configured to: (1) receive the vital signs data related to a vital sign of the individual, (2) process the vital signs data to generate a vital signs related risk score indicating a variable bed fall risk of the individual wherein processing the vital signs data comprises detecting at least one risk factor from the vital signs data, (3) receive profile information about the individual, (4) process the profile information to generate an intrinsic risk score indicating an intrinsic bed fall risk of the individual, and (5) combine the vital signs related risk score and the intrinsic risk score to generate a combined final risk score comprising the bed fall risk of the individual.

2. The device according to claim 1, wherein the processing unit is further configured to assign a reliability value to said vital signs data and/or said vital signs related risk score, and to determine a variable risk score of the individual from the reliability value and the vital signs risk score.

3. The device according to claim 1, wherein the risk factor is a psychogenic status such as tension or stress, anxiety, restlessness, and agitation, and/or a posture, such as raising of the torso, leaning over the bed edge, and reaching out of bed.

4. The device according to claim 1, wherein the vital signs data comprises one or more of accelerometer data, heart rate monitoring data, heart rate variability monitoring data, and respiration monitoring data.

5. The device according to claim 4, wherein the processing unit is further configured to obtain accelerometer data in channels corresponding to spatial directions x, y, z, wherein the x direction is oriented along a length of a bed where the individual is located in, the z direction is oriented along the width of the bed, and the y direction is oriented along an axis perpendicular to a plane of the bed spanned by the x and z directions.

6. The device according to claim 5, wherein the processing unit is further configured to detect tension or stress and anxiety of the individual located in the bed by observing heart rate monitoring data, respiration monitoring data, heart rate variability monitoring data and/or accelerometer data in a predetermined time window, and wherein the heart rate monitoring data, respiration monitoring data, and/or heart rate variability monitoring data surpass predetermined values, and wherein the accelerometer data are below a predetermined value in all spatial directions x, y, z.

7. The device according to claim 5, wherein the processing unit is further configured to detect the posture of the individual located in the bed by detecting, counting, and analyzing the accelerometer data in the channels according to the spatial directions x, y, z.

8. The device according to claim 5, wherein the processing unit is further configured to detect restlessness or agitation of the individual located in the bed by observing heart rate monitoring data, respiration monitoring data, heart rate variability monitoring data and accelerometer data in a predetermined time window, wherein the heart rate monitoring data, respiration monitoring data, heart rate variability monitoring data surpass predetermined values and the accelerometer data of at least one channel corresponding to the spatial directions x, y, z surpass a predetermined threshold.

9. The device according to claim 8, wherein the accelerometer data of the channels corresponding to the x and z direction surpass the predetermined threshold and the accelerometer data of the y direction is below the predetermined threshold for the risk factor of restlessness.

10. The device according to claim 8, wherein the accelerometer data of the channels corresponding to the x and y direction surpass the predetermined threshold and the accelerometer data of the z direction is below the predetermined threshold for the risk factor of agitation.

11. The device according to claim 2, wherein the processing unit is further configured to determine the vital signs risk score and/or the reliability value at discrete intervals or continually.

12. The device according to claim 1, wherein the vital signs sensor is at least one of an accelerometer, a photoplethysmography sensor, a heart rate monitor, a blood pressure monitor, an $SpO_2$ sensor, and a respiration monitor.

13. A method for determination of a bed fall risk of an individual, the method comprising the steps of:
obtaining sensor data related to a vital sign of an individual;
processing the vital signs data to generate a vital signs related risk score indicating a variable bed fall risk of the individual by detecting at least one risk factor from the vital signs data and computing the vital signs risk score from the at least one risk factor;
obtaining profile information about the individual;
processing the profile information to generate an intrinsic risk score indicating an intrinsic bed fall risk of the individual; and
combining the vital signs related risk score and the intrinsic risk score to generate a combined final risk score comprising the bed fall risk of the individual.

14. A non-transitory computer-readable medium comprising program code for causing a computer to carry out the steps of the method as claimed in claim 13 when said computer program is carried out on a computer.

15. The method according to claim 13, further comprising the steps of assigning a reliability value to said vital signs data and/or said vital signs related risk score, and determining a variable risk score of the individual from the reliability value and the vital signs risk score.

16. The method according to claim 13, wherein the risk factor is a psychogenic status such as tension or stress, anxiety, restlessness, and agitation, and/or a posture such as raising of the torso, leaning over the bed edge, and reaching out of bed.

17. The method according to claim 13, wherein the vital signs data comprises one or more of accelerometer data, heart rate monitoring data, heart rate variability monitoring data, and respiration monitoring data.

18. The method according to claim 17, further comprising the step of obtaining accelerometer data in channels corresponding to spatial directions x, y, z, wherein the x direction is oriented along a length of a bed where the individual is located in, the z direction is oriented along the width of the bed, and the y direction is oriented along an axis perpendicular to a plane of the bed spanned by the x and z directions.

19. The method according to claim 18, further comprising the step of detecting tension or stress and anxiety of the individual located in the bed by observing heart rate monitoring data, respiration monitoring data, heart rate variability monitoring data and/or accelerometer data in a predetermined time window, and wherein the heart rate monitoring data, respiration monitoring data, and/or heart rate variability monitoring data surpass predetermined values, and wherein the accelerometer data are below a predetermined value in all spatial directions x, y, z.

* * * * *